(12) United States Patent
Bolduc

(10) Patent No.: US 9,320,589 B2
(45) Date of Patent: Apr. 26, 2016

(54) ENDOVASCULAR ANEURYSM REPAIR SYSTEM

(75) Inventor: Lee Bolduc, Fremont, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 240 days.

(21) Appl. No.: 13/162,384

(22) Filed: Jun. 16, 2011

(65) Prior Publication Data

US 2012/0065661 A1    Mar. 15, 2012

Related U.S. Application Data

(62) Division of application No. 11/166,411, filed on Jun. 24, 2005, now Pat. No. 8,092,519, which is a division of application No. 10/271,334, filed on Oct. 15, 2002, now Pat. No. 6,960,217.

(60) Provisional application No. 60/333,937, filed on Nov. 28, 2001.

(51) Int. Cl.
*A61F 2/06* (2013.01)
*A61B 17/064* (2006.01)
(Continued)

(52) U.S. Cl.
CPC .............. *A61F 2/06* (2013.01); *A61B 17/064* (2013.01); *A61B 17/068* (2013.01); *A61F 2/07* (2013.01); *A61B 2017/0646* (2013.01); *A61B 2017/0649* (2013.01); *A61F 2/064* (2013.01); *A61F 2/848* (2013.01); *A61F 2/90* (2013.01);
(Continued)

(58) Field of Classification Search
CPC ........... A61B 2017/0649; A61B 17/10; A61B 17/115; A61B 17/064; A61B 17/068; A61B 2017/1157; A61B 2017/06446

USPC .......................... 606/108, 155, 157; 623/1.11
See application file for complete search history.

(56) References Cited

U.S. PATENT DOCUMENTS

| 2,033,039 A | 3/1936 | Limpert |
| 3,499,222 A | 3/1970 | Linkow et al. |

(Continued)

FOREIGN PATENT DOCUMENTS

| AU | 2002353807 B2 | 6/2003 |
| AU | 2004277897 B2 | 4/2005 |

(Continued)

OTHER PUBLICATIONS

Anonymous. (1995). "5mm Origin Tacker™ It Runs in Circles Around Staples," *Guidant Origin Advertising Literature*, 2 pages.

(Continued)

*Primary Examiner* — David C Eastwood
*Assistant Examiner* — Martin T Ton

(57) ABSTRACT

Method and apparatus for implanting radially expandable prostheses in the body lumens rely on tacking or anchoring of the prostheses with separately introduced fasteners. The prostheses may be self-expanding or balloon expandable. After initial placement, a fastener applier system is introduced within the expanded prostheses to deploy a plurality of fasteners at least one prosthesis end, usually as each end of the prosthesis. The fasteners are usually helical fasteners which are delivered from a helical track in the fastener applier by rotation with a rotator wire. The fasteners will be applied singly, typically in circumferentially spaced-apart patterns about the interior of each end of the prosthesis.

12 Claims, 19 Drawing Sheets

(51) Int. Cl.
  *A61B 17/068* (2006.01)
  *A61F 2/07* (2013.01)
  *A61F 2/848* (2013.01)
  *A61F 2/90* (2013.01)

(52) U.S. Cl.
  CPC .... *A61F 2002/061* (2013.01); *A61F 2002/065* (2013.01); *A61F 2002/067* (2013.01); *A61F 2002/075* (2013.01); *Y10S 623/903* (2013.01)

(56) References Cited

U.S. PATENT DOCUMENTS

| | | |
|---|---|---|
| 3,686,740 A | 8/1972 | Shiley |
| 3,799,172 A | 3/1974 | Szpur |
| 4,140,126 A | 2/1979 | Choudhury |
| 4,255,820 A | 3/1981 | Rothermel et al. |
| 4,307,722 A | 12/1981 | Evans |
| 4,580,568 A | 4/1986 | Gianturco |
| 4,586,923 A | 5/1986 | Gould et al. |
| 4,625,597 A | 12/1986 | Cast |
| 4,694,827 A | 9/1987 | Weiner et al. |
| 4,781,682 A | 11/1988 | Patel |
| 4,822,345 A | 4/1989 | Danforth |
| 4,898,577 A | 2/1990 | Badger et al. |
| 4,899,747 A | 2/1990 | Garren et al. |
| 4,921,484 A | 5/1990 | Hillstead |
| 4,990,151 A | 2/1991 | Wallsten |
| 4,994,071 A | 2/1991 | MacGregor |
| 5,030,204 A | 7/1991 | Badger et al. |
| 5,042,707 A | 8/1991 | Taheri |
| 5,044,519 A | 9/1991 | Aoyama |
| 5,071,407 A | 12/1991 | Termin et al. |
| 5,104,399 A | 4/1992 | Lazarus |
| 5,185,004 A | 2/1993 | Lashinski et al. |
| 5,192,314 A | 3/1993 | Daskalakis |
| 5,195,968 A | 3/1993 | Lundquist et al. |
| 5,199,950 A | 4/1993 | Schmitt et al. |
| 5,207,695 A | 5/1993 | Trout, III |
| 5,282,824 A | 2/1994 | Gianturco |
| 5,290,295 A | 3/1994 | Querals et al. |
| 5,318,525 A | 6/1994 | West et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,352,197 A | 10/1994 | Hammersmark et al. |
| 5,364,351 A | 11/1994 | Heinzelman et al. |
| 5,383,880 A | 1/1995 | Hooven et al. |
| 5,387,235 A | 2/1995 | Chuter |
| 5,409,498 A | 4/1995 | Braddock et al. |
| 5,456,713 A | 10/1995 | Chuter |
| 5,456,714 A | 10/1995 | Owen |
| 5,470,337 A | 11/1995 | Moss |
| 5,474,568 A | 12/1995 | Scott |
| 5,480,382 A | 1/1996 | Hammerslag et al. |
| 5,480,423 A | 1/1996 | Ravenscroft et al. |
| 5,489,295 A | 2/1996 | Piplani et al. |
| 5,522,881 A | 6/1996 | Lentz |
| 5,531,686 A | 7/1996 | Lundquist et al. |
| 5,534,007 A | 7/1996 | St. Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A * | 12/1996 | Bolduc et al. .............. 606/143 |
| 5,591,195 A | 1/1997 | Taheri et al. |
| 5,609,627 A | 3/1997 | Goicoechea et al. |
| 5,626,613 A | 5/1997 | Schmieding |
| 5,628,788 A | 5/1997 | Pinchuk |
| 5,632,772 A | 5/1997 | Alcime et al. |
| 5,634,936 A | 6/1997 | Linden et al. |
| 5,639,278 A | 6/1997 | Dereume et al. |
| 5,662,675 A | 9/1997 | Polanskyj Stockert et al. |
| 5,662,683 A * | 9/1997 | Kay .............. 606/232 |
| 5,662,700 A | 9/1997 | Lazarus |
| 5,676,696 A | 10/1997 | Marcade |
| 5,676,697 A | 10/1997 | McDonald |
| 5,683,450 A | 11/1997 | Goicoechea et al. |
| 5,693,084 A | 12/1997 | Chuter |
| 5,693,086 A | 12/1997 | Goicoechea et al. |
| 5,700,269 A | 12/1997 | Pinchuk et al. |
| 5,702,343 A | 12/1997 | Alferness |
| 5,702,365 A | 12/1997 | King |
| 5,702,408 A | 12/1997 | Wales et al. |
| 5,707,376 A | 1/1998 | Kavteladze et al. |
| 5,713,907 A | 2/1998 | Bogendijk et al. |
| 5,733,325 A | 3/1998 | Robinson et al. |
| 5,749,921 A | 5/1998 | Lenker et al. |
| 5,755,777 A | 5/1998 | Chuter |
| 5,762,458 A | 6/1998 | Wang et al. |
| 5,769,884 A | 6/1998 | Solovay |
| 5,776,142 A | 7/1998 | Gunderson |
| 5,779,731 A | 7/1998 | Leavitt |
| 5,782,844 A * | 7/1998 | Yoon et al. .............. 606/139 |
| 5,797,933 A | 8/1998 | Snow et al. |
| 5,800,528 A | 9/1998 | Lederman et al. |
| 5,810,882 A | 9/1998 | Bolduc et al. |
| 5,814,016 A | 9/1998 | Valley et al. |
| 5,824,008 A | 10/1998 | Bolduc et al. |
| 5,824,037 A | 10/1998 | Fogarty et al. |
| 5,824,041 A | 10/1998 | Lenker et al. |
| 5,830,221 A | 11/1998 | Stein et al. |
| 5,830,229 A | 11/1998 | Konya et al. |
| 5,843,160 A | 12/1998 | Rhodes |
| 5,855,565 A | 1/1999 | Bar-Cohen et al. |
| 5,855,598 A | 1/1999 | Pinchuk |
| 5,861,003 A | 1/1999 | Latson et al. |
| 5,865,791 A | 2/1999 | Whayne |
| 5,876,432 A | 3/1999 | Lau et al. |
| 5,904,713 A | 5/1999 | Leschinsky |
| 5,906,619 A | 5/1999 | Olson et al. |
| 5,906,641 A | 5/1999 | Thompson et al. |
| 5,916,263 A | 6/1999 | Goicoechea et al. |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,003 A * | 10/1999 | Rousseau et al. ............. 606/142 |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 5,997,556 A | 12/1999 | Tanner |
| 6,016,810 A | 1/2000 | Ravenscroft |
| 6,024,703 A | 2/2000 | Zanelli et al. |
| 6,024,763 A | 2/2000 | Lenker et al. |
| 6,027,462 A | 2/2000 | Greene et al. |
| 6,070,589 A | 6/2000 | Keith et al. |
| 6,074,418 A | 6/2000 | Buchanan et al. |
| 6,077,214 A | 6/2000 | Mortier et al. |
| 6,077,297 A | 6/2000 | Robinson et al. |
| 6,086,582 A | 7/2000 | Altman et al. |
| 6,090,137 A | 7/2000 | Schmitt |
| 6,123,722 A | 9/2000 | Fogarty et al. |
| 6,126,685 A | 10/2000 | Lenker et al. |
| 6,129,685 A | 10/2000 | Howard, III |
| 6,145,509 A | 11/2000 | Tanner |
| 6,146,339 A | 11/2000 | Biagtan et al. |
| 6,152,144 A | 11/2000 | Lesh et al. |
| 6,162,168 A | 12/2000 | Schweich, Jr. et al. |
| 6,168,610 B1 | 1/2001 | Marin et al. |
| 6,174,323 B1 | 1/2001 | Biggs et al. |
| 6,179,809 B1 | 1/2001 | Khairkhahan et al. |
| 6,197,049 B1 | 3/2001 | Shaolian et al. |
| 6,203,550 B1 | 3/2001 | Olson |
| 6,203,568 B1 | 3/2001 | Lombardi et al. |
| 6,206,827 B1 | 3/2001 | Chin et al. |
| 6,217,597 B1 | 4/2001 | Tanner |
| 6,224,540 B1 | 5/2001 | Lederman et al. |
| 6,231,561 B1 | 5/2001 | Frazier et al. |
| 6,248,118 B1 | 6/2001 | Tanner et al. |
| 6,250,974 B1 | 6/2001 | Kerek |
| 6,258,021 B1 | 7/2001 | Wilk |
| 6,258,119 B1 | 7/2001 | Hussein et al. |
| 6,270,516 B1 | 8/2001 | Tanner et al. |

(56) References Cited

U.S. PATENT DOCUMENTS

| | | |
|---|---|---|
| 6,273,858 B1 | 8/2001 | Fox et al. |
| 6,286,514 B1 | 9/2001 | Lemelson |
| 6,287,315 B1 | 9/2001 | Wijeratne et al. |
| 6,287,335 B1 | 9/2001 | Drasler et al. |
| 6,293,906 B1 | 9/2001 | Vanden Hoek et al. |
| 6,296,656 B1 | 10/2001 | Bolduc et al. |
| 6,302,906 B1 | 10/2001 | Goicoechea et al. |
| 6,309,403 B1 | 10/2001 | Minor et al. |
| 6,319,278 B1 | 11/2001 | Quinn |
| 6,336,933 B1 | 1/2002 | Parodi |
| 6,343,605 B1 | 2/2002 | Lafontaine |
| 6,346,118 B1 | 2/2002 | Baker et al. |
| 6,352,561 B1 | 3/2002 | Leopold et al. |
| 6,361,556 B1 | 3/2002 | Chuter |
| 6,368,345 B1 | 4/2002 | Dehdashtian et al. |
| 6,371,919 B1 | 4/2002 | Tanner et al. |
| 6,398,803 B1 | 6/2002 | Layne et al. |
| 6,402,680 B2 | 6/2002 | Mortier et al. |
| 6,402,780 B2 | 6/2002 | Williamson, IV et al. |
| 6,406,420 B1 | 6/2002 | McCarthy et al. |
| 6,409,757 B1 | 6/2002 | Trout, III et al. |
| 6,416,365 B1 | 7/2002 | Iwahori |
| 6,416,522 B1 | 7/2002 | Strecker |
| 6,423,059 B1 | 7/2002 | Hanson et al. |
| 6,425,856 B1 | 7/2002 | Shapland et al. |
| 6,428,565 B1 | 8/2002 | Wisselink |
| 6,454,796 B1 | 9/2002 | Barkman et al. |
| 6,458,152 B1 | 10/2002 | Khosravi et al. |
| 6,461,365 B2 | 10/2002 | Bolduc et al. |
| 6,468,260 B1 | 10/2002 | Bumbalough et al. |
| 6,482,224 B1 | 11/2002 | Michler et al. |
| 6,520,974 B2 * | 2/2003 | Tanner et al. .............. 606/153 |
| 6,544,253 B1 | 4/2003 | Tanner |
| 6,558,425 B2 | 5/2003 | Rockwood, Jr. |
| 6,562,051 B1 | 5/2003 | Bolduc et al. |
| 6,565,597 B1 | 5/2003 | Fearnot et al. |
| 6,576,009 B2 | 6/2003 | Ryan et al. |
| 6,580,417 B2 | 6/2003 | Rosenberg et al. |
| 6,592,593 B1 * | 7/2003 | Parodi et al. .............. 606/108 |
| 6,592,615 B1 | 7/2003 | Marcade et al. |
| 6,595,912 B2 | 7/2003 | Lau et al. |
| 6,607,555 B2 | 8/2003 | Patterson et al. |
| 6,616,684 B1 | 9/2003 | Vidlund et al. |
| 6,639,278 B2 | 10/2003 | Sumida et al. |
| 6,652,555 B1 | 11/2003 | Vantassel et al. |
| 6,652,572 B2 | 11/2003 | Kugler et al. |
| 6,663,558 B2 | 12/2003 | Lau et al. |
| 6,675,809 B2 | 1/2004 | Stack et al. |
| 6,685,620 B2 | 2/2004 | Gifford, III et al. |
| 6,702,763 B2 | 3/2004 | Murphy et al. |
| 6,702,844 B1 | 3/2004 | Lazarus |
| 6,709,442 B2 | 3/2004 | Miller et al. |
| 6,719,174 B1 | 4/2004 | Swift |
| 6,730,119 B1 | 5/2004 | Smalling |
| 6,746,460 B2 | 6/2004 | Gannoe et al. |
| 6,800,081 B2 | 10/2004 | Parodi |
| 6,878,164 B2 | 4/2005 | Kujawski et al. |
| 6,929,661 B2 | 8/2005 | Bolduc et al. |
| 6,960,217 B2 | 11/2005 | Bolduc |
| 6,984,241 B2 | 1/2006 | Lubbers et al. |
| 6,986,775 B2 | 1/2006 | Morales et al. |
| 6,986,784 B1 | 1/2006 | Weiser et al. |
| 7,033,384 B2 | 4/2006 | Gannoe et al. |
| 7,037,343 B2 | 5/2006 | Imran |
| 7,060,021 B1 | 6/2006 | Wilk |
| 7,060,023 B2 | 6/2006 | French et al. |
| 7,081,086 B2 | 7/2006 | Lau et al. |
| 7,081,129 B2 | 7/2006 | Chobotov |
| 7,128,754 B2 | 10/2006 | Bolduc |
| 7,147,657 B2 | 12/2006 | Chiang et al. |
| 7,155,295 B2 | 12/2006 | Lau et al. |
| 7,179,225 B2 | 2/2007 | Shluzas et al. |
| 7,306,623 B2 | 12/2007 | Watson |
| 7,335,213 B1 | 2/2008 | Hyde et al. |
| 7,361,137 B2 | 4/2008 | Taylor et al. |
| 7,404,824 B1 | 7/2008 | Webler et al. |
| 7,422,558 B2 | 9/2008 | Lau et al. |
| 7,491,232 B2 | 2/2009 | Bolduc et al. |
| 7,544,198 B2 | 6/2009 | Parodi et al. |
| 7,563,267 B2 | 7/2009 | Goldfarb et al. |
| 7,591,842 B2 | 9/2009 | Parodi |
| 7,637,932 B2 | 12/2009 | Bolduc et al. |
| 7,704,269 B2 | 4/2010 | St. Goar et al. |
| 7,727,189 B2 | 6/2010 | Vantassel et al. |
| 7,753,922 B2 | 7/2010 | Starksen |
| 7,811,295 B2 | 10/2010 | Kortenbach |
| 7,823,267 B2 | 11/2010 | Bolduc et al. |
| 7,828,838 B2 | 11/2010 | Bolduc et al. |
| 7,959,663 B2 | 6/2011 | Bolduc |
| 7,959,670 B2 | 6/2011 | Bolduc |
| 8,075,570 B2 | 12/2011 | Bolduc et al. |
| 8,080,050 B2 | 12/2011 | Chiang et al. |
| 8,083,752 B2 | 12/2011 | Bolduc |
| 8,092,519 B2 | 1/2012 | Bolduc |
| 8,231,639 B2 | 7/2012 | Bolduc et al. |
| 8,685,044 B2 | 4/2014 | Bolduc et al. |
| 8,690,897 B2 | 4/2014 | Bolduc |
| 9,023,065 B2 | 5/2015 | Bolduc et al. |
| 2001/0041821 A1 | 11/2001 | Wilk |
| 2001/0047199 A1 | 11/2001 | Wijay |
| 2002/0026144 A1 | 2/2002 | Patterson |
| 2002/0029077 A1 | 3/2002 | Leopold et al. |
| 2002/0058855 A1 | 5/2002 | Schweich, Jr. et al. |
| 2002/0065485 A1 | 5/2002 | DuBois et al. |
| 2002/0087169 A1 | 7/2002 | Brock et al. |
| 2002/0099432 A1 | 7/2002 | Yee |
| 2002/0133054 A1 | 9/2002 | Murphy et al. |
| 2002/0156365 A1 | 10/2002 | Tsekos |
| 2002/0156521 A1 | 10/2002 | Ryan et al. |
| 2002/0183827 A1 | 12/2002 | Derus et al. |
| 2003/0018358 A1 | 1/2003 | Saadat |
| 2003/0060674 A1 | 3/2003 | Gifford, III et al. |
| 2003/0078465 A1 | 4/2003 | Pai et al. |
| 2003/0100943 A1 | 5/2003 | Bolduc |
| 2003/0105384 A1 | 6/2003 | Sharkey et al. |
| 2003/0105519 A1 | 6/2003 | Fasol et al. |
| 2003/0130731 A1 | 7/2003 | Vidlund et al. |
| 2003/0149463 A1 | 8/2003 | Solymar et al. |
| 2003/0158570 A1 | 8/2003 | Ferrazzi |
| 2003/0163085 A1 | 8/2003 | Tanner et al. |
| 2003/0204249 A1 | 10/2003 | Letort |
| 2003/0233140 A1 | 12/2003 | Hartley et al. |
| 2004/0002731 A1 | 1/2004 | Aganon et al. |
| 2004/0039405 A1 | 2/2004 | Petrovic et al. |
| 2004/0044364 A1 | 3/2004 | Devries et al. |
| 2004/0049207 A1 | 3/2004 | Goldfarb et al. |
| 2004/0054352 A1 | 3/2004 | Adams et al. |
| 2004/0093057 A1 | 5/2004 | Bolduc et al. |
| 2004/0127916 A1 | 7/2004 | Bolduc et al. |
| 2004/0138734 A1 | 7/2004 | Chobotov et al. |
| 2004/0153143 A1 | 8/2004 | Quiachon et al. |
| 2004/0186566 A1 | 9/2004 | Hindrichs et al. |
| 2004/0206363 A1 | 10/2004 | Mccarthy et al. |
| 2004/0210304 A1 | 10/2004 | Seguin et al. |
| 2004/0243170 A1 | 12/2004 | Suresh et al. |
| 2004/0254594 A1 | 12/2004 | Alfaro |
| 2004/0260322 A1 | 12/2004 | Rudko et al. |
| 2004/0260383 A1 | 12/2004 | Stelter et al. |
| 2005/0038506 A1 | 2/2005 | Webler et al. |
| 2005/0043790 A1 | 2/2005 | Seguin |
| 2005/0070992 A1 | 3/2005 | Bolduc et al. |
| 2005/0113906 A9 | 5/2005 | Bolduc et al. |
| 2005/0154401 A1 | 7/2005 | Weldon et al. |
| 2005/0177180 A1 | 8/2005 | Kaganov et al. |
| 2005/0187613 A1 | 8/2005 | Bolduc |
| 2005/0197716 A1 | 9/2005 | Sharkey et al. |
| 2005/0215874 A1 | 9/2005 | Wang et al. |
| 2005/0240258 A1 | 10/2005 | Bolduc et al. |
| 2005/0240260 A1 | 10/2005 | Bolduc |
| 2006/0100640 A1 | 5/2006 | Bolduc et al. |
| 2006/0111692 A1 | 5/2006 | Hlavka et al. |
| 2006/0184224 A1 | 8/2006 | Angel |
| 2006/0253186 A1 | 11/2006 | Bates |
| 2006/0259125 A1 | 11/2006 | Peacock, III |

(56) References Cited

U.S. PATENT DOCUMENTS

| | | |
|---|---|---|
| 2006/0287661 A1 | 12/2006 | Bolduc et al. |
| 2007/0021753 A1 | 1/2007 | Bolduc et al. |
| 2007/0021829 A1 | 1/2007 | Bolduc et al. |
| 2007/0032860 A1 | 2/2007 | Brooks et al. |
| 2007/0073389 A1 | 3/2007 | Bolduc et al. |
| 2007/0083255 A1 | 4/2007 | Chiang et al. |
| 2008/0065117 A1 | 3/2008 | Bolduc et al. |
| 2008/0065189 A1 | 3/2008 | Bolduc |
| 2008/0065191 A1 | 3/2008 | Bolduc et al. |
| 2008/0097489 A1 | 4/2008 | Goldfarb et al. |
| 2008/0132996 A1 | 6/2008 | Drasler et al. |
| 2009/0082852 A1 | 3/2009 | Bolduc et al. |
| 2009/0099650 A1 | 4/2009 | Bolduc et al. |
| 2009/0112302 A1 | 4/2009 | Stafford |
| 2009/0112303 A1 | 4/2009 | Bolduc |
| 2009/0138072 A1 | 5/2009 | Gendreau |
| 2010/0094400 A1 | 4/2010 | Bolduc et al. |
| 2011/0087320 A1 | 4/2011 | Bolduc et al. |
| 2011/0238088 A1 | 9/2011 | Bolduc et al. |
| 2011/0276062 A1 | 11/2011 | Bolduc |
| 2012/0316578 A1 | 12/2012 | Bolduc et al. |
| 2014/0194902 A1 | 7/2014 | Bolduc et al. |
| 2014/0214051 A1 | 7/2014 | Bolduc |
| 2015/0127015 A1 | 5/2015 | Bolduc et al. |

FOREIGN PATENT DOCUMENTS

| | | |
|---|---|---|
| AU | 2005235108 A1 | 11/2005 |
| AU | 2008243229 A1 | 12/2008 |
| AU | 2004287355 B2 | 6/2011 |
| AU | 2006305688 B2 | 12/2012 |
| AU | 2011253682 B9 | 1/2014 |
| AU | 2011224089 B2 | 7/2014 |
| CA | 2265131 A1 | 9/1999 |
| CA | 2344252 A1 | 3/2000 |
| CA | 2729464 A1 | 6/2003 |
| CA | 2539265 A1 | 5/2005 |
| CA | 2626505 A1 | 4/2007 |
| CA | 2626106 A1 | 5/2007 |
| CA | 2625082 A1 | 7/2008 |
| CA | 2740831 A1 | 4/2010 |
| CA | 2464048 A1 | 6/2010 |
| CA | 2464900 A1 | 4/2011 |
| CA | 2554022 A1 | 11/2012 |
| CA | 2546721 C | 9/2013 |
| CN | 1019461 B | 12/1992 |
| CN | 1422139 A | 6/2003 |
| CN | 1596087 A | 3/2005 |
| CN | 1596088 A | 3/2005 |
| CN | 1856280 A | 11/2006 |
| CN | 1870949 A | 11/2006 |
| CN | 1870951 A | 11/2006 |
| CN | 1997318 A | 7/2007 |
| CN | 101151002 A | 3/2008 |
| CN | 101267788 A | 9/2008 |
| CN | 101330882 A | 12/2008 |
| CN | 101352375 A | 1/2009 |
| CN | 101360466 A | 2/2009 |
| CN | 101460104 A | 6/2009 |
| CN | 101466316 A | 6/2009 |
| CN | 100525719 C | 8/2009 |
| CN | 101330882 B | 4/2011 |
| CN | 101466316 B | 6/2012 |
| DE | 3333427 C2 | 5/1991 |
| DE | 69228184 T2 | 9/1999 |
| DE | 10034105 C1 | 4/2002 |
| DE | 10297483 T5 | 12/2004 |
| EP | 0 321 912 A1 | 6/1989 |
| EP | 0 663 184 A1 | 7/1995 |
| EP | 0835642 B1 | 2/2002 |
| EP | 1 369 098 A1 | 12/2003 |
| EP | 1 440 673 A1 | 7/2004 |
| EP | 1448117 A1 | 8/2004 |
| EP | 1675528 A2 | 7/2006 |
| EP | 1725172 A2 | 11/2006 |
| EP | 1734872 A1 | 12/2006 |
| EP | 1948080 A2 | 7/2008 |
| EP | 2119416 A1 | 11/2009 |
| EP | 2349086 A1 | 8/2011 |
| EP | 2349087 A1 | 8/2011 |
| FR | 2299548 A1 | 8/1976 |
| FR | 2865926 A1 | 8/2005 |
| GB | 2396824 A | 7/2004 |
| GB | 2417208 A | 2/2006 |
| HK | 1073240 A1 | 8/2009 |
| JP | 2001509398 A | 7/2001 |
| JP | 2001522292 A | 11/2001 |
| JP | 2001-526574 A | 12/2001 |
| JP | 2002526193 A | 8/2002 |
| JP | 2005046648 A | 2/2005 |
| JP | 2005510293 A | 4/2005 |
| JP | 2005510303 A | 4/2005 |
| JP | 2007508894 A | 4/2007 |
| JP | 2007508895 A | 4/2007 |
| JP | 2007523694 A | 8/2007 |
| JP | 2007535339 A | 12/2007 |
| JP | 2009512497 A | 3/2009 |
| JP | 2009512498 A | 3/2009 |
| JP | 2009512499 A | 3/2009 |
| JP | 2009078172 A | 4/2009 |
| JP | 2009095684 A | 5/2009 |
| JP | 2009106763 A | 5/2009 |
| JP | 2009106768 A | 5/2009 |
| JP | 2009106775 A | 5/2009 |
| JP | 2009112827 A | 5/2009 |
| JP | 2009519046 A | 5/2009 |
| JP | 4405262 B2 | 1/2010 |
| JP | 10506026 A | 2/2010 |
| JP | 2010051786 A | 3/2010 |
| JP | 4465359 B2 | 5/2010 |
| JP | 2011062570 A | 3/2011 |
| JP | 4699445 B2 | 6/2011 |
| WO | WO-9300868 A1 | 1/1993 |
| WO | WO-9521592 A1 | 8/1995 |
| WO | WO-9603925 A1 | 2/1996 |
| WO | WO-97/03616 A1 | 2/1997 |
| WO | WO-9703616 A1 | 2/1997 |
| WO | WO-9712562 A1 | 4/1997 |
| WO | WO-9717039 A1 | 5/1997 |
| WO | WO-9717913 A1 | 5/1997 |
| WO | WO-9811814 A2 | 3/1998 |
| WO | WO-98/53761 A1 | 12/1998 |
| WO | WO-9930637 A1 | 6/1999 |
| WO | WO-9933402 A1 | 7/1999 |
| WO | WO-9933402 A9 | 9/1999 |
| WO | WO-99/53845 A1 | 10/1999 |
| WO | WO-9953845 A1 | 10/1999 |
| WO | WO-0064357 A1 | 1/2000 |
| WO | WO-00/16701 A1 | 3/2000 |
| WO | WO-00/35350 A1 | 6/2000 |
| WO | WO-0160432 A1 | 8/2001 |
| WO | WO-03032870 A1 | 4/2003 |
| WO | WO-03/045283 A1 | 6/2003 |
| WO | WO-03/045467 A2 | 6/2003 |
| WO | WO-03/045467 A3 | 6/2003 |
| WO | WO-03/079935 A1 | 10/2003 |
| WO | WO-2004008975 A1 | 1/2004 |
| WO | WO-2004021872 A2 | 3/2004 |
| WO | WO-2005/032333 A2 | 4/2005 |
| WO | WO-2005/032333 A3 | 4/2005 |
| WO | WO-2005037076 A2 | 4/2005 |
| WO | WO-2005/044073 A2 | 5/2005 |
| WO | WO-2005/044073 A3 | 5/2005 |
| WO | WO-2005044147 A1 | 5/2005 |
| WO | WO-2005044148 A1 | 5/2005 |
| WO | WO-2005/067660 A2 | 7/2005 |
| WO | WO-2005081936 A2 | 9/2005 |
| WO | WO-2005102181 A1 | 11/2005 |
| WO | WO-2007/046955 A2 | 4/2007 |
| WO | WO-2007/046955 A3 | 4/2007 |
| WO | WO-2007/047023 A2 | 4/2007 |
| WO | WO-2007/047023 A3 | 4/2007 |
| WO | WO-2005067660 A3 | 4/2007 |

(56) References Cited

FOREIGN PATENT DOCUMENTS

| WO | WO-2007046953 A2 | 4/2007 |
|---|---|---|
| WO | WO-2007046954 A2 | 4/2007 |
| WO | WO-2007053233 A2 | 5/2007 |
| WO | WO-2007046953 A3 | 6/2007 |
| WO | WO-2005081936 A3 | 11/2007 |
| WO | WO-2007053233 A3 | 1/2008 |
| WO | WO-2007046954 A3 | 11/2008 |
| WO | WO-2010004856 A1 | 1/2010 |
| WO | WO-2010044851 A1 | 4/2010 |
| WO | WO-2010044854 A1 | 4/2010 |
| WO | WO-2010044855 A1 | 4/2010 |
| WO | WO-2010044856 A1 | 4/2010 |

OTHER PUBLICATIONS

Gadacz, T. et al. (Nov. 1995). "The Spiral Tacker: A New Technique for Stabilizing Prosthetic Mesh in Laparoscopic Hernia Repair," *Surgical Rounds* 461-467.
Medical Technologies. (Oct. 1995). "Laparoscopic Surgery," *Medical Data International, Inc. MedPro* p. 190.
Newman, L. et al. (1995). "Tacker-Assisted TAPP Procedure," Circa, 2 pages.
Hatchett, R.L. et al. (1995). "Extraperitoneal Endoscopic Burch Repair Using a Tacker Mesh Technique," Circa 1-4.
Non-final Office Action mailed May 18, 2004, for U.S. Appl. No. 10/271,334, filed Oct. 15, 2002, 8 pages.
Examiner's Interview Summary mailed Feb. 11, 2005, for U.S. Appl. No. 10/271,334, filed Oct. 15, 2002, 1 page.
Non-Final Office Action mailed Oct. 6, 2008, for U.S. Appl. No. 11/540,427, filed Sep. 29, 2006, 9 pages.
Final Office Action mailed Jul. 21, 2009, for U.S. Appl. No. 11/540,427, filed Sep. 29, 2006, 8 pages.
Non-Final Office Action mailed May 20, 2010, for U.S. Appl. No. 11/978,752, filed Oct. 30, 2007, 5 pages.
Final Office Action mailed Dec. 22, 2010, for U.S. Appl. No. 11/978,752, filed Oct. 30, 2007, 6 pages.
Non-Final Office Action mailed Sep. 3, 2010, for U.S. Appl. No. 11/978,753, filed Oct. 30, 2007, 7 pages.
Non-Final Office Action mailed Jan. 27, 2006, for U.S. Appl. No. 10/669,881, filed Sep. 24, 2003, 5 pages.
Final Office Action mailed Jan. 25, 2008, for U.S. Appl. No. 10/669,881, filed Sep. 24, 2003, 7 pages.
Notice of Allowance mailed Oct. 8, 2008, for U.S. Appl. No. 10/669,881, filed Sep. 24, 2003, 6 pages.
Notice of Allowance mailed Mar. 9, 2010, for U.S. Appl. No. 11/254,444, filed Oct. 20, 2005, 6 pages.
Notice of Allowance mailed Jun. 29, 2010, for U.S. Appl. No. 11/254,444, filed Oct. 20, 2005, 6 pages.
Non-Final Office Action mailed Oct. 1, 2009, for U.S. Appl. No. 11/254,619, filed Oct. 20, 2005, 5 pages.
Final Office Action mailed Jun. 30, 2010, for U.S. Appl. No. 11/254,619, filed Oct. 20, 2005, 10 pages.
Non-Final Office Action mailed Feb. 3, 2011, for U.S. Appl. No. 11/254,619, filed Oct. 20, 2005, 8 pages.
Non-Final Office Action mailed Mar. 30, 2009, for U.S. Appl. No. 11/254,950, filed Oct. 20, 2005, 5 pages.
Notice of Allowance mailed Feb. 26, 2010, for U.S. Appl. No. 11/254,950, filed Oct. 20, 2005, 4 pages.
Notice of Allowance mailed Jun. 22, 2010, for U.S. Appl. No. 11/254,950, filed Oct. 20, 2005, 4 pages.
Non-Final Office Action mailed May 14, 2008, for U.S. Appl. No. 11/255,116, filed Oct. 20, 2005, 14 pages.
Notice of Allowance mailed Aug. 10, 2009, for U.S. Appl. No. 11/255,116, filed Oct. 20, 2005, 4 pages.
Non-Final Office Action mailed Sep. 1, 2010, for U.S. Appl. No. 11/488,305, filed Jul. 18, 2006, 7 pages.
International Search Report mailed Jul. 8, 2008, for PCT Patent Application No. PCT/US2006/033747, filed on Aug. 29, 2006, published on Apr. 26, 2007, as WO 2007/046954, 2 pages.
Written Opinion mailed Jul. 8, 2008, for PCT Patent Application No. PCT/US2006/033747, filed on Aug. 29, 2006, published on Apr. 26, 2007, as WO 2007/046954, 3 pages.
International Search Report mailed on Feb. 24, 2006, for PCT Patent Application No. PCT/US2004/029402, filed on Sep. 10, 2004, published on Apr. 14, 2005, as WO 2005/032333, 3 pages.
Written Opinion mailed on Feb. 24, 2006, for PCT Patent Application No. PCT/US2004/029402, filed on Sep. 10, 2004, published on Apr. 14, 2005, as WO 2005/032333, 3 pages.
International Preliminary Report on Patentability mailed on Jul. 10, 2006, for PCT Patent Application No. PCT/US2004/029402, filed on Sep. 10, 2004, published on Apr. 14, 2005, as WO 2005/032333, 3 pages.
International Search Report mailed on Mar. 30, 2007, for PCT Patent Application No. PCT/US2006/033741, filed on Aug. 29, 2006, published on Apr. 26, 2007, as WO 2007/046953, 2 pages.
Written Opinion mailed on Mar. 30, 2007, for PCT Patent Application No. PCT/US2006/033741, filed on Aug. 29, 2006, published on Apr. 26, 2007, as WO 2007/046953, 4 pages.
International Preliminary Examination Report mailed on Jul. 28, 2007, for PCT Patent Application No. PCT/US2006/033741, filed on Aug. 29, 2006, published on Apr. 26, 2007, as WO 2007/046953, 5 pages.
International Search Report mailed on Aug. 15, 2007, for PCT Patent Application No. PCT/US2006/033748, filed on Aug. 29, 2006, published on May 10, 2007, as WO 2007/053233, 3 pages.
Written Opinion mailed on Aug. 15, 2007, for PCT Patent Application No. PCT/US2006/033748, filed on Aug. 29, 2006, published on May 10, 2007, as WO 2007/053233, 5 pages.
International Preliminary Report on Patentability mailed on Jun. 18, 2008, for PCT Patent Application No. PCT/US2006/033748, filed on Aug. 29, 2006, published on May 10, 2007, as WO 2007/053233, 7 pages.
International Search Report mailed on Aug. 15, 2007, for PCT Patent Application No. PCT/US06/033749, filed on Aug. 29, 2006, published on Apr. 26, 2007, as WO 2007/046955, 3 pages.
Written Opinion mailed on Aug. 15, 2007, for PCT Patent Application No. PCT/US06/033749, filed on Aug. 29, 2006, published on Apr. 26, 2007, as WO 2007/046955, 5 pages.
International Preliminary Report on Patentability mailed on Jun. 18, 2008, for PCT Patent Application No. PCT/US06/033749, filed on Aug. 29, 2006, published on Apr. 26, 2007, as WO 2007/046955, 6 pages.
International Search Report mailed on Mar. 6, 2003, for PCT Patent Application No. PCT/US02/32753, filed on Oct. 15, 2002, published on Jun. 5, 2003, as WO 2003/045283, one page.
Written Opinion mailed on Aug. 26, 2003, for PCT Patent Application No. PCT/US02/32753, filed on Oct. 15, 2002, published on Jun. 5, 2003, as WO 2003/045283, 4 pages.
International Preliminary Report on Patentability mailed on Sep. 1, 2004, for PCT Patent Application No. PCT/US02/32753, filed on Oct. 15, 2002, published on Jun. 5, 2003, as WO 2003/045283, 3 pages.
International Search Report mailed on May 8, 2003, for PCT Patent Application No. PCT/US02/38365, filed on Nov. 29, 2002, published on Jun. 5, 2003, as WO 2003/045467, 4 pages.
Written Opinion mailed on Oct. 27, 2003, for PCT Patent Application No. PCT/US02/38365, filed on Nov. 29, 2002, published on Jun. 5, 2003, as WO 2003/045467, 4 pages.
International Preliminary Report on Patentability mailed on Mar. 1, 2004, for PCT Patent Application No. PCT/US02/38365, filed on Nov. 29, 2002, published on Jun. 5, 2003, as WO 2003/045467, 3 pages.
International Search Report mailed on Aug. 30, 2007, for PCT/US2006/037085, filed on Sep. 22, 2006, published on Apr. 26, 2007, as WO 2007/047023, one page.
Written Opinion mailed on Aug. 30, 2007, for PCT/US2006/037085, filed on Sep. 22, 2006, published on Apr. 26, 2007, as WO 2007/047023, 7 pages.
International Preliminary Report on Patentability mailed on Jul. 24, 2008, for PCT/US2006/037085, filed on Sep. 22, 2006, published on Apr. 26, 2007, as WO 2007/047023, 9 pages.

(56) References Cited

OTHER PUBLICATIONS

Notice of Allowability mailed on Feb. 11, 2005, for U.S. Appl. No. 10/271,334, filed Oct. 15, 2002, 4 pages.
Notice of Allowance mailed on Mar. 17, 2005, for U.S. Appl. No. 10/271,334, filed Oct. 15, 2002, 3 pages.
Notice of Allowance mailed on Aug. 26, 2005, for U.S. Appl. No. 10/271,334, filed Oct. 15, 2002, 3 pages.
Non Final Office Action mailed on May 5, 2009, for U.S. Appl. No. 11/166,411, filed Jun. 24, 2005, 7 pages.
Final Office Action mailed on Dec. 3, 2009, for U.S. Appl. No. 11/166,411, filed Jun. 24, 2005, 5 pages.
Notice of Allowance mailed on Jan. 6, 2011, for U.S. Appl. No. 11/166,411, filed Jun. 24, 2005, 4 pages.
Notice of Allowance mailed Apr. 29, 2011, for U.S. Appl. No. 11/540,427, filed Sep. 29, 2006, 8 pages.
Final Office Action mailed May 2, 2011, for U.S. Appl. No. 11/978,753, filed Oct. 30, 2007, 8 pages.
Final Office Action mailed on Apr. 13, 2011, for U.S. Appl. No. 11/488,305, filed Jul. 18, 2006, 8 pages.
U.S. Appl. No. 11/978,753, filed Oct. 30, 2007, Systems and Methods for Applying Tissue-Piercing Fasteners.
U.S. Appl. No. 11/166,428, filed Jun. 24, 2005, Multi-Lumen Prosthesis Systems and Methods.
U.S. Appl. No. 13/495,836, filed Jun. 13, 2012, Systems and Methods for Attaching a Prosthesis Within a Body Lumen or Hollow Organ.
U.S. Appl. No. 12/315,015, filed Nov. 26, 2008, Catheter-Based Fastener Implantation Apparatus and Methods.
U.S. Appl. No. 11/540,428, filed Sep. 29, 2006, Catheter-Based Fastener Implantation Apparatus and Methods.
U.S. Appl. No. 11/254,619, filed Oct. 20, 2005, Devices, System, and Methods for Guiding an Operative Tool Into an Interior Body Region.
U.S. Appl. No. 12/942,232, filed Nov. 9, 2010, Devices, Systems and Methods for Prosthesis Delivery and Implementation, Including a Prosthesis Assembly.
U.S. Appl. No. 10/808,216, filed Mar. 24, 2004, Devices, Systems, and Methods for Supporting Tissue and/or Structures Within a Hollow Body Organ.
U.S. Appl. No. 11/365,056, filed Mar. 1, 2006, Devices, Systems, and Methods for Supporting Tissue and/or Structures Within a Hollow Body Organ.
U.S. Appl. No. 13/157,242, filed Jun. 9, 2011, Devices, Systems, and Methods for Supporting Tissue and/or Structures Within a Hollow Body Organ.
U.S. Appl. No. 12/917,842, filed Nov. 2, 2010, Devices, Systems, and Methods for Prosthesis Delivery and Implantation, Including the Use of a Fastener Tool.
U.S. Appl. No. 12/653,219, filed Dec. 10, 2009, Devices, Systems, and Methods for Prosthesis Delivery and Implantation.
U.S. Appl. No. 11/488,305, filed Jul. 18, 2006, Endovascular Aneurysm Devices, Systems, and Methods.
U.S. Appl. No. 12/288,031, filed Oct. 16, 2008, Devices, Systems, and Methods for Endovascular Staple and/or Prosthesis Delivery and Implantation.
U.S. Appl. No. 12/288,034, filed Oct. 16, 2008, Devices, Systems, and Methods for Endovascular Staple and/or Prosthesis Delivery and Implantation.
U.S. Appl. No. 10/752,435, filed Jan. 6, 2004, Prosthesis Systems and Methods Sized and Configured for the Receipt and Retention of Fasteners.
U.S. Appl. No. 11/981,112, filed Oct. 31, 2007, Prosthesis Systems and Methods.
U.S. Appl. No. 12/288,045, filed Oct. 16, 2008, Devices, Systems, and Methods for Endovascular Staple and/or Prosthesis Delivery and Implantation.
U.S. Appl. No. 12/288,032, filed Oct. 16, 2008, Devices, Systems, and Methods for Endovascular Staple and/or Prosthesis Delivery and Implantation.
U.S. Appl. No. 10/307,226, Final Office Action mailed Dec. 12, 2006, 6 pgs.
U.S. Appl. No. 10/307,226, Non Final Office Action mailed Mar. 13, 2006, 7 pgs.
U.S. Appl. No. 10/307,226, Non Final Office Action mailed Jun. 12, 2007, 6 pgs.
U.S. Appl. No. 10/307,226, Non Final Office Action mailed Sep. 9, 2009, 6 pgs.
U.S. Appl. No. 10/693,255, Examiner Interview Summary mailed Feb. 17, 2005, 3 pgs.
U.S. Appl. No. 10/693,255, Non Final Office Action mailed Dec. 9, 2004, 6 pgs.
U.S. Appl. No. 10/693,255, Notice of Allowance mailed Mar. 9, 2005, 9 pgs.
U.S. Appl. No. 10/786,465, Final Office Action mailed Jan. 21, 2009, 8 pgs.
U.S. Appl. No. 10/786,465, Non Final Office Action mailed Mar. 26, 2010, 8 pgs.
U.S. Appl. No. 10/786,465, Non Final Office Action mailed Jul. 23, 2007, 7 pgs.
U.S. Appl. No. 10/786,465, Notice of Allowance mailed Mar. 14, 2012, 11 pgs.
U.S. Appl. No. 11/166,411, Notice of Allowance mailed Aug. 23, 2011, 5 pgs.
U.S. Appl. No. 11/254,619, Final Office Action mailed Oct. 20, 2011, 12 pgs.
U.S. Appl. No. 11/488,305, Advisory Action mailed Jun. 7, 2013, 3 pgs.
U.S. Appl. No. 11/488,305, Final Office Action mailed Mar. 6, 2013, 9 pgs.
U.S. Appl. No. 11/488,305, Non Final Office Action mailed Sep. 14, 2012, 9 pgs.
U.S. Appl. No. 11/488,305, Non Final Office Action mailed Oct. 31, 2011, 6 pgs.
U.S. Appl. No. 11/488,305, Response filed Feb. 1, 2011 to Non Final Office Action mailed Sep. 1, 2010, 12 pgs.
U.S. Appl. No. 11/488,305, Response filed Feb. 13, 2013 to Non Final Office Action mailed Sep. 14, 2012, 10 pgs.
U.S. Appl. No. 11/488,305, Response filed Apr. 26, 2012 to Non Final Office Action mailed Oct. 31, 2011, 12 pgs.
U.S. Appl. No. 11/488,305, Response filed May 3, 2013 to Final Office Action mailed Mar. 6, 2013, 11 pgs.
U.S. Appl. No. 11/488,305, Response filed Jul. 2, 2010 to Restriction Requirement mailed Jan. 5, 2010, 8 pgs.
U.S. Appl. No. 11/488,305, Response filed Oct. 13, 2011 to Final Office Action mailed Apr. 13, 2011, 11 pgs.
U.S. Appl. No. 11/488,305, Restriction Requirement mailed Jan. 5, 2010, 6 pgs.
U.S. Appl. No. 11/540,428, Final Office Action mailed Aug. 4, 2011, 9 pgs.
U.S. Appl. No. 11/540,428, Non Final Office Action mailed Nov. 12, 2010, 8 pgs.
U.S. Appl. No. 11/978,752, Notice of Allowance mailed Aug. 31, 2011, 5 pgs.
U.S. Appl. No. 11/978,753, Non Final Office Action mailed Sep. 3, 2010, 8 pgs.
U.S. Appl. No. 12/288,031, Advisory Action mailed Apr. 12, 2013, 3 pgs.
U.S. Appl. No. 12/288,031, Final Office Action mailed Jan. 3, 2012, 9 pgs.
U.S. Appl. No. 12/315,015, Final Office Action mailed Apr. 26, 2012, 7 pgs.
U.S. Appl. No. 12/315,015, Non Final Office Action mailed Oct. 6, 2011, 11 pgs.
U.S. Appl. No. 12/653,219, Non Final Office Action mailed May 30, 2012, 16 pgs.
U.S. Appl. No. 12/917,842, filed Nov. 2, 2010, 120 pgs.
U.S. Appl. No. 12/917,842, Non Final Office Action mailed Nov. 13, 2012, 6 pgs.
U.S. Appl. No. 12/917,842, Notice of Allowance mailed May 20, 2013, 8 pgs.
U.S. Appl. No. 12/917,842, Notice of Allowance mailed Aug. 31, 2011, 5 pgs.
U.S. Appl. No. 12/917,842, Response filed Apr. 15, 2013 to Non Final Office Action mailed Nov. 13, 2012, 9 pgs.

(56) References Cited

OTHER PUBLICATIONS

U.S. Appl. No. 12/917,842, Response filed Oct. 15, 2012 to Restriction Requirement mailed Sep. 14, 2012, 2 pgs.
U.S. Appl. No. 12/917,842, Restriction Requirement mailed Sep. 14, 2012, 5 pgs.
U.S. Appl. No. 13/157,242, Final Office Action mailed May 16, 2013, 7 pgs.
U.S. Appl. No. 13/162,384, Preliminary Amendment filed Jun. 16, 2011, 7 pgs.
U.S. Appl. No. 13/495,836, Non Final Office Action mailed Dec. 26, 2012, 9 pgs.
Australian Application Serial No. 2011224089, First Examiners Report mailed Mar. 27, 2013, 3 pgs.
Australian Application Serial No. 2011253682, Office Action mailed Sep. 27, 2012, 4 pgs.
Canadian Application Serial No. 2,626,403, Office Action mailed Apr. 2, 2013, 3 pgs.
International Application Serial No. PCT/US2005/005627, International Preliminary Examination Report mailed Apr. 7, 2009, 3 pgs.
International Application Serial No. PCT/US2005/005627, International Search Report mailed Sep. 25, 2007, 1 pg.
International Application Serial No. PCT/US2005/005627, Written Opinion mailed Sep. 25, 2007, 3 pgs.
International Application Serial No. PCT/US2009/005604, International Search Report mailed Dec. 11, 2009, 2 pgs.
International Application Serial No. PCT/US2009/005604, Written Opinion mailed Dec. 11, 2009, 7 pgs.
International Application Serial No. PCT/US2009/005609, International Search Report mailed Dec. 18, 2009, 2 pgs.
International Application Serial No. PCT/US2009/005609, Written Opinion mailed Dec. 18, 2009, 6 pgs.
U.S. Appl. No. 10/271,334, Examiner Interview Summary mailed Feb. 11, 2005, 2 pgs.
U.S. Appl. No. 10/271,334, Non Final Office Action mailed May 18, 2004, 9 pgs.
U.S. Appl. No. 10/271,334, Notice of Allowance mailed Feb. 11, 2005, 6 pgs.
U.S. Appl. No. 10/271,334, Notice of Allowance mailed Aug. 26, 2005, 3 pgs.
U.S. Appl. No. 10/271,334, Response filed Mar. 15, 2004 to Restriction Requirement mailed Sep. 23, 2003, 1 pg.
U.S. Appl. No. 10/271,334, Response filed Nov. 22, 2004 to Non Final Office Action mailed May 18, 2004, 6 pgs.
U.S. Appl. No. 10/271,334, Restriction Requirement mailed Sep. 23, 2003, 4 pgs.
U.S. Appl. No. 10/271,334, Supplemental Response filed Jan. 28, 2005 to Non Final Office Action mailed May 18, 2004, 6 pgs.
U.S. Appl. No. 10/307,226, 312 Amendment filed Oct. 24, 2011, 3 pgs.
U.S. Appl. No. 10/307,226, Appeal Brief filed Oct. 14, 2010, 15 pgs.
U.S. Appl. No. 10/307,226, Final Office Action mailed Jun. 27, 2008, 6 pgs.
U.S. Appl. No. 10/307,226, Final Office Action mailed Dec. 12, 2006, 5 pgs.
U.S. Appl. No. 10/307,226, Non Final Office Action mailed Mar. 13, 2006, 6 pgs.
U.S. Appl. No. 10/307,226, Non Final Office Action mailed Jun. 12, 2007, 5 pgs.
U.S. Appl. No. 10/307,226, Non Final Office Action mailed Sep. 9, 2009, 16 pgs.
U.S. Appl. No. 10/307,226, Notice of Allowance mailed Jul. 22, 2011, 8 pgs.
U.S. Appl. No. 10/307,226, Preliminary Amendment filed Jul. 22, 2005, 3 pgs.
U.S. Appl. No. 10/307,226, PTO Response to 312 Amendment mailed Nov. 10, 2011, 3 pgs.
U.S. Appl. No. 10/307,226, Response filed Apr. 9, 2007 to Final Office Action mailed Dec. 12, 2006, 7 pgs.
U.S. Appl. No. 10/307,226, Response filed Jun. 23, 2009 to Final Office Action mailed Jun. 27, 2008, 10 pgs.
U.S. Appl. No. 10/307,226, Response filed Sep. 15, 2006 to Non Final Office Action mailed Mar. 13, 2006, 6 pgs.
U.S. Appl. No. 10/307,226, Response filed Dec. 14, 2007 to Non Final Office Action mailed Jun. 12, 2007, 7 pgs.
U.S. Appl. No. 10/669,881, Final Office Action mailed Jan. 25, 2008, 7 pgs.
U.S. Appl. No. 10/669,881, Non Final Office Action mailed Jan. 27, 2006, 5 pgs.
U.S. Appl. No. 10/669,881, Notice of Allowance mailed Oct. 8, 2008, 16 pgs.
U.S. Appl. No. 10/669,881, Preliminary Amendment May 6, 2005, 3 pgs.
U.S. Appl. No. 10/669,881, Response filed Mar. 11, 2008 to Final Office Action mailed Jan. 25, 2008, 8 pgs.
U.S. Appl. No. 10/669,881, Response filed May 15, 2006 to Non Final Office Action mailed Jan. 27, 2006, 9 pgs.
U.S. Appl. No. 10/669,881, Response filed Sep. 7, 2007 to Restriction Requirement mailed Jun. 19, 2007, 4 pgs.
U.S. Appl. No. 10/669,881, Response filed Oct. 2, 2006 to Restriction Requirement mailed Jul. 27, 2006, 6 pgs.
U.S. Appl. No. 10/669,881, Restriction Requirement Jul. 27, 2006, 5 pgs.
U.S. Appl. No. 10/669,881, Restriction Requirement mailed Jun. 19, 2007, 5 pgs.
U.S. Appl. No. 10/692,282, Non Final Office Action mailed Aug. 30, 2005, 6 pgs.
U.S. Appl. No. 10/692,282, Notice of Allowance mailed Jun. 13, 2006, 6 pgs.
U.S. Appl. No. 10/692,282, Response filed Feb. 22, 2005 to Restriction Requirement mailed Aug. 17, 2004, 4 pgs.
U.S. Appl. No. 10/692,282, Response filed Feb. 28, 2006 to Non Final Office Action mailed Aug. 30, 2005, 5 pgs.
U.S. Appl. No. 10/692,282, Restriction Requirement mailed Aug. 17, 2004, 6 pgs.
U.S. Appl. No. 10/693,255, Response filed Feb. 17, 2005 to Non Final Office Action mailed Dec. 9, 2004, 6 pgs.
U.S. Appl. No. 10/752,435, Final Office Action mailed May 14, 2010, 8 pgs.
U.S. Appl. No. 10/752,435, Final Office Action mailed Jul. 12, 2007, 8 pgs.
U.S. Appl. No. 10/752,435, Final Office Action mailed Dec. 8, 2008, 8 pgs.
U.S. Appl. No. 10/752,435, Non Final Office Action mailed Mar. 18, 2008, 7 pgs.
U.S. Appl. No. 10/752,435, Non Final Office Action mailed Jul. 21, 2009, 7 pgs.
U.S. Appl. No. 10/752,435, Non Final Office Action mailed Oct. 19, 2006, 17 pgs.
U.S. Appl. No. 10/752,435, Response filed Jan. 9, 2008 to Final Office Action mailed Jul. 12, 2007, 10 pgs.
U.S. Appl. No. 10/752,435, Response filed Jan. 25, 2010 to Non Final Office Action mailed Jul. 21, 2009, 9 pgs.
U.S. Appl. No. 10/752,435, Response filed Apr. 9, 2007 to Non Final Office Action mailed Oct. 19, 2006, 13 pgs.
U.S. Appl. No. 10/752,435, Response filed May 12, 2009 to Final Office Action mailed Dec. 8, 2008, 9 pgs.
U.S. Appl. No. 10/752,435, Response filed Sep. 19, 2008 to Non Final Office Action mailed Mar. 18, 2008, 7 pgs.
U.S. Appl. No. 10/786,465, Applicant's Summary of Examiner Interview filed Jun. 6, 2012, 2 pgs.
U.S. Appl. No. 10/786,465, Corrected Notice of Allowability mailed Jul. 2, 2012, 4 pgs.
U.S. Appl. No. 10/786,465, Examiner Interview Summary mailed Mar. 3, 2008, 2 pgs.
U.S. Appl. No. 10/786,465, Examiner Interview Summary mailed Apr. 26, 2011, 3 pgs.
U.S. Appl. No. 10/786,465, Preliminary Amendment filed May 16, 2005, 3 pgs.
U.S. Appl. No. 10/786,465, Response filed Jan. 25, 2008 to Non Final Office Action mailed Jul. 23, 2007, 8 pgs.
U.S. Appl. No. 10/786,465, Response filed Apr. 9, 2007 to Restriction Requirement mailed Dec. 8, 2006, 4 pgs.

(56) References Cited

OTHER PUBLICATIONS

U.S. Appl. No. 10/786,465, Response filed Apr. 26, 2011 to Non Final Office Action mailed Mar. 26, 2010, 14 pgs.
U.S. Appl. No. 10/786,465, Response filed Jul. 22, 2009 to Final Office Action mailed Jan. 21, 2009, 5 pgs.
U.S. Appl. No. 10/786,465, Response filed Sep. 19, 2008 to Restriction Requirement mailed Jul. 24, 2008, 4 pgs.
U.S. Appl. No. 10/786,465, Restriction Requirement mailed Jul. 24, 2008, 5 pgs.
U.S. Appl. No. 10/786,465, Restriction Requirement mailed Dec. 8, 2006, 6 pgs.
U.S. Appl. No. 10/786,465, Supplemental Amendment filed Mar. 18, 2008, 8 pgs.
U.S. Appl. No. 10/786,465, Supplemental Notice of Allowability mailed May 8, 2012, 6 pgs.
U.S. Appl. No. 10/808,216, Preliminary Amendment filed Jun. 15, 2005, 3 pgs.
U.S. Appl. No. 11/166,411, 312 Amendment filed Nov. 23, 2011, 3 pgs.
U.S. Appl. No. 11/166,411, Final Office Action mailed Dec. 3, 2009, 5 pgs.
U.S. Appl. No. 11/166,411, Non Final Office Action mailed May 5, 2009, 8 pgs.
U.S. Appl. No. 11/166,411, Preliminary Amendment filed Oct. 2, 2006, 5 pgs.
U.S. Appl. No. 11/166,411, PTO Response to 312 Amendment mailed Dec. 13, 2011, 2 pgs.
U.S. Appl. No. 11/166,411, Response filed Jan. 12, 2009 to Restriction Requirement mailed Jul. 15, 2008, 5 pgs.
U.S. Appl. No. 11/166,411, Response filed Jun. 7, 2010 to Final Office Action mailed Dec. 3, 2009, 5 pgs.
U.S. Appl. No. 11/166,411, Response filed Nov. 9, 2009 to Non Final Office Action mailed May 5, 2009, 8 pgs.
U.S. Appl. No. 11/166,411, Restriction Requirement mailed Jul. 15, 2008, 5 pgs.
U.S. Appl. No. 11/166,411, Supplemental Preliminary Amendment filed Oct. 30, 2007, 7 pgs.
U.S. Appl. No. 11/166,428, Final Office Action mailed Jan. 12, 2009, 10 pgs.
U.S. Appl. No. 11/166,428, Final Office Action mailed Mar. 16, 2010, 8 pgs.
U.S. Appl. No. 11/166,428, Non Final Office Action mailed May 14, 2008, 6 pgs.
U.S. Appl. No. 11/166,428, Non Final Office Action mailed Jun. 16, 2009, 10 pgs.
U.S. Appl. No. 11/166,428, Response filed May 12, 2009 to Final Office Action mailed Jan. 12, 2009, 6 pgs.
U.S. Appl. No. 11/166,428, Response filed Nov. 17, 2008 to Non Final Office Action mailed May 14, 2008, 6 pgs.
U.S. Appl. No. 11/166,428, Response filed Dec. 22, 2009 to Non Final Office Action mailed Dec. 16, 2009, 8 pgs.
U.S. Appl. No. 11/254,444, Notice of Allowance mailed Apr. 5, 2010, 4 pgs.
U.S. Appl. No. 11/254,444, Preliminary Amendment filed Oct. 20, 2005, 8 pgs.
U.S. Appl. No. 11/254,444, Preliminary Amendment filed Nov. 15, 2005, 8 pgs.
U.S. Appl. No. 11/254,444, Response filed Dec. 18, 2009 to Restriction Requirement mailed Jun. 19, 2009, 2 pgs.
U.S. Appl. No. 11/254,444, Restriction Requirement mailed Jun. 19, 2009, 6 pgs.
U.S. Appl. No. 11/254,619, Non Final Office Action mailed Jan. 6, 2014, 19 pgs.
U.S. Appl. No. 11/254,619, Response filed Apr. 1, 2010 to Non Final Office Action mailed Oct. 1, 2009, 5 pgs.
U.S. Appl. No. 11/254,619, Response filed Apr. 20, 2012 to Final Office Action mailed Oct. 20, 2011, 11 pgs.
U.S. Appl. No. 11/254,619, Response filed Aug. 3, 2011 to Non Final Office Action mailed Feb. 3, 2011, 13 pgs.
U.S. Appl. No. 11/254,619, Response filed Dec. 29, 2010 to Final Office Action mailed Jun. 30, 2010, 12 pgs.
U.S. Appl. No. 11/254,950, Preliminary Amendment filed Nov. 18, 2005, 4 pgs.
U.S. Appl. No. 11/254,950, Response filed Jan. 5, 2009 to Restriction Requirement mailed Jul. 9, 2008, 7 pgs.
U.S. Appl. No. 11/254,950, Response filed Oct. 5, 2009 to Non Final Office Action mailed Mar. 30, 2009, 5 pgs.
U.S. Appl. No. 11/254,950, Restriction Requirement mailed Jul. 9, 2008, 9 pgs.
U.S. Appl. No. 11/255,116, Preliminary Amendment filed Nov. 18, 2005, 4 pgs.
U.S. Appl. No. 11/255,116, Response filed May 20, 2009 to Restriction Requirement mailed Mar. 18, 2009, 4 pgs.
U.S. Appl. No. 11/255,116, Response filed Nov. 17, 2008 to Non Final Office Action mailed May 24, 2008, 7 pgs.
U.S. Appl. No. 11/255,116, Restriction Requirement mailed Mar. 18, 2009, 7 pgs.
U.S. Appl. No. 11/365,056, Final Office Action mailed Dec. 9, 2010, 13 pgs.
U.S. Appl. No. 11/365,056, Non Final Office Action mailed Mar. 23, 2010, 11 pgs.
U.S. Appl. No. 11/365,056, Response filed Sep. 28, 2010 to Non Final Office Action mailed Mar. 23, 2010, 5 pgs.
U.S. Appl. No. 11/365,056, Response filed Dec. 10, 2009 to Restriction Requirement mailed Jun. 10, 2009, 44 pgs.
U.S. Appl. No. 11/365,056, Restriction Requirement mailed Jun. 10, 2009, 5 pgs.
U.S. Appl. No. 11/488,305, Non Final Office Action mailed Jan. 29, 2014, 10 pgs.
U.S. Appl. No. 11/540,427, Appeal Brief filed Aug. 26, 2010, 26 pgs.
U.S. Appl. No. 11/540,427, Notice of Allowance mailed Apr. 11, 2011, 8 pgs.
U.S. Appl. No. 11/540,427, Preliminary Amendment filed Oct. 3, 2007, 5 pgs.
U.S. Appl. No. 11/540,427, Response filed Apr. 10, 2009 to Non Final Office Action mailed Oct. 6, 2008, 6 pgs.
U.S. Appl. No. 11/540,428, Response filed May 12, 2011 to Non Final Office Action mailed Nov. 12, 2010, 12 pgs.
U.S. Appl. No. 11/540,428, Response filed Oct. 1, 2010 to Restriction Requirement mailed Mar. 29, 2010, 6 pgs.
U.S. Appl. No. 11/540,428, Restriction Requirement mailed Mar. 29, 2010, 9 pgs.
U.S. Appl. No. 11/580,584, Appeal Brief filed Nov. 15, 2010, 11 pgs.
U.S. Appl. No. 11/580,584, Final Office Action mailed Jan. 22, 2009, 9 pgs.
U.S. Appl. No. 11/580,584, Final Office Action mailed Oct. 16, 2009, 8 pgs.
U.S. Appl. No. 11/580,584, Non Final Office Action mailed Apr. 18, 2008, 6 pgs.
U.S. Appl. No. 11/580,584, Notice of Allowance mailed Feb. 4, 2011, 7 pgs.
U.S. Appl. No. 11/580,584, Response filed Jul. 22, 2009 to Final Office Action mailed Jan. 22, 2009, 6 pgs.
U.S. Appl. No. 11/580,584, Response filed Oct. 20, 2008 to Non Final Office Action mailed Apr. 18, 2008, 5 pgs.
U.S. Appl. No. 11/978,752, Response filed May 10, 2010 to Restriction Requirement mailed Nov. 6, 2009, 4 pgs.
U.S. Appl. No. 11/978,752, Response filed Jun. 22, 2011 to Final Office Action mailed Dec. 22, 2010, 6 pgs.
U.S. Appl. No. 11/978,752, Response filed Nov. 5, 2010 to Non Final Office Action mailed May 20, 2010, 4 pgs.
U.S. Appl. No. 11/978,752, Restriction Requirement mailed Nov. 6, 2009, 7 pgs.
U.S. Appl. No. 11/978,753, Response filed Mar. 3, 2011 to Non Final Office Action mailed Sep. 3, 2010, 9 pgs.
U.S. Appl. No. 11/981,112, Advisory Action mailed Jan. 31, 2014, 3 pgs.
U.S. Appl. No. 11/981,112, Final Office Action mailed Apr. 29, 2010, 9 pgs.
U.S. Appl. No. 11/981,112, Final Office Action mailed Oct. 8, 2013, 9 pgs.

(56) References Cited

OTHER PUBLICATIONS

U.S. Appl. No. 11/981,112, Non Final Office Action mailed Feb. 28, 2014, 9 pgs.
U.S. Appl. No. 11/981,112, Non Final Office Action mailed Jul. 8, 2009, 11 pgs.
U.S. Appl. No. 11/981,112, Response file dJan. 8, 2014 to Final Office Action mailed Oct. 8, 2013, 11 pgs.
U.S. Appl. No. 11/981,112, Response filed Jan. 6, 2010 to Non Final Office Action mailed Jul. 8, 2009, 7 pgs.
U.S. Appl. No. 11/981,112, Response filed Nov. 1, 2010 to Final Office Action mailed Apr. 29, 2010, 7 pgs.
U.S. Appl. No. 12/288,031, Final Office Action mailed Mar. 12, 2014, 14 pgs.
U.S. Appl. No. 12/288,031, Non Final Office Action mailed May 10, 2012, 8 pgs.
U.S. Appl. No. 12/288,031, Non Final Office Action mailed Jul. 15, 2013, 9 pgs.
U.S. Appl. No. 12/288,031, Response filed Mar. 25, 2013 to Final Office Action mailed Jan. 3, 2013, 11 pgs.
U.S. Appl. No. 12/288,031, Response filed Apr. 4, 2012 to Restriction Requirement mailed Nov. 4, 2011, 3 pgs.
U.S. Appl. No. 12/288,031, Response filed Oct. 10, 2012 to Non Final Office Action mailed May 10, 2012, 11 pgs.
U.S. Appl. No. 12/288,031, Response filed Nov. 15, 2013 to Non Final Office Action mailed Jul. 15, 2013, 11 pgs.
U.S. Appl. No. 12/288,031, Restriction Requirement mailed Nov. 4, 2011, 9 pgs.
U.S. Appl. No. 12/288,032, Restriction Requirement mailed Nov. 4, 2011, 9 pgs.
U.S. Appl. No. 12/288,034, Advisory Action mailed Feb. 25, 2014, 3 pgs.
U.S. Appl. No. 12/288,034, Final Office Action mailed Nov. 4, 2013, 8 pgs.
U.S. Appl. No. 12/288,034, Non Final Office Action mailed Jun. 22, 2012, 7 pgs.
U.S. Appl. No. 12/288,034, Response filed Feb. 4, 2014 to Final Office Action mailed Nov. 4, 2013, 12 pgs.
U.S. Appl. No. 12/288,034, Response filed May 1, 2012 to Restriction Requirement mailed Nov. 3, 2011, 4 pgs.
U.S. Appl. No. 12/288,034, Response filed Dec. 21, 2012 to Non Final Office Action mailed Jun. 22, 2012, 12 pgs.
U.S. Appl. No. 12/288,034, Restriction Requirement mailed Nov. 3, 2011, 9 pgs.
U.S. Appl. No. 12/288,045, Restriction Requirement mailed Nov. 16, 2011, 9 pgs.
U.S. Appl. No. 12/315,015, Advisory Action mailed Apr. 7, 2014, 3 pgs.
U.S. Appl. No. 12/315,015, Advisory Action mailed Sep. 12, 2012, 3 pgs.
U.S. Appl. No. 12/315,015, Final Office Action mailed Jan. 28, 2014, 8 pgs.
U.S. Appl. No. 12/315,015, Non Final Office Action mailed Sep. 27, 2013, 7 pgs.
U.S. Appl. No. 12/315,015, Preliminary Amendment filed Mar. 10, 2009, 3 pgs.
U.S. Appl. No. 12/315,015, Response filed Mar. 28, 2014 to Final Office Action mailed Jan. 24, 2014, 5 pgs.
U.S. Appl. No. 12/315,015, Response filed Apr. 6, 2012 to Non Final Office Action mailed Oct. 6, 2011, 12 pgs.
U.S. Appl. No. 12/315,015, Response filed Aug. 27, 2012 to Final Office Action mailed Apr. 26, 2012, 6 pgs.
U.S. Appl. No. 12/315,015, Response filed Dec. 27, 2013 to Non Final Office Action mailed Sep. 27, 2013, 7 pgs.
U.S. Appl. No. 12/917,842, Notice of Allowance mailed Aug. 27, 2013, 6 pgs.
U.S. Appl. No. 12/917,842, Notice of Allowance mailed Dec. 2, 2013, 7 pgs.
U.S. Appl. No. 12/942,232, Non Final Office Action mailed Oct. 9, 2013, 13 pgs.
U.S. Appl. No. 12/942,232, Response filed Jan. 9, 2014 to Non Final Office Action mailed Oct. 9, 2013, 11 pgs.
U.S. Appl. No. 13/157,242, Advisory Action mailed Jul. 30, 2013, 3 pgs.
U.S. Appl. No. 13/157,242, Non Final Office Action mailed Jun. 18, 2012, 9 pgs.
U.S. Appl. No. 13/157,242, Non Final Office Action mailed Oct. 31, 2013, 6 pgs.
U.S. Appl. No. 13/157,242, Notice of Allowance mailed Feb. 26, 2014, 8 pgs.
U.S. Appl. No. 13/157,242, Preliminary Amendment filed Jun. 9, 2011, 7 pgs.
U.S. Appl. No. 13/157,242, Response filed Jan. 28, 2014 to Non Final Office Action mailed Oct. 31, 2013, 11 pgs.
U.S. Appl. No. 13/157,242, Response filed Jun. 1, 2012 to Restriction Requirement mailed May 1, 2012, 3 pgs.
U.S. Appl. No. 13/157,242, Response filed Jul. 16, 2013 to Final Office Action mailed May 16, 2013, 9 pgs.
U.S. Appl. No. 13/157,242, Response filed Dec. 18, 2012 to Non Final Office Action mailed Jun. 18, 2012, 11 pgs.
U.S. Appl. No. 13/157,242, Restriction Requirement mailed May 1, 2012, 6 pgs.
U.S. Appl. No. 13/495,836, Non Final Office Action mailed Aug. 5, 2013, 7 pgs.
U.S. Appl. No. 13/495,836, Notice of Allowance mailed Dec. 4, 2013, 9 pgs.
U.S. Appl. No. 13/495,836, Preliminary Amendment filed Jun. 13, 2012, 8 pgs.
U.S. Appl. No. 13/495,836, Response filed Mar. 25, 2013 to Non Final Office Action mailed Dec. 26, 2012, 9 pgs.
U.S. Appl. No. 13/495,836, Response filed Nov. 5, 2013 to Non Final Office Action mailed Aug. 5, 2013, 8 pgs.
Australian Application Serial No. 2002351188, Office Action mailed Mar. 30, 2007, 1 pg.
Australian Application Serial No. 2002351188, Office Action mailed Dec. 8, 2008, 3 pgs.
Australian Application Serial No. 2002353807, First Examiner Report mailed Nov. 16, 2006, 2 pgs.
Australian Application Serial No. 2004277897, First Examiner Report mailed Oct. 14, 2009, 2 pgs.
Australian Application Serial No. 2004277897, Response filed Jul. 14, 2011 to First Examiner Report mailed Oct. 14, 2009, 9 pgs.
Australian Application Serial No. 2004287354, Office Action mailed Oct. 13, 2009, 2 pgs.
Australian Application Serial No. 2004287355, Office Action mailed May 11, 2009, 2 pgs.
Australian Application Serial No. 2005204615, Office Action mailed Jan. 20, 2010, 4 pgs.
Australian Application Serial No. 2005235108, Office Action mailed Feb. 26, 2010, 3 pgs.
Australian Application Serial No. 2006302908, Office Action mailed Mar. 4, 2011, 8 pgs.
Australian Application Serial No. 2006305688, First Examiner Report mailed Mar. 10, 2011, 3 pgs.
Australian Application Serial No. 2006305688, Response filed Oct. 22, 2012 to First Examiner Report mailed Mar. 10, 2011, 16 pgs.
Australian Application Serial No. 2006305689, Office Action mailed Sep. 5, 2011, 3 pgs.
Australian Application Serial No. 2006309241, Office Action mailed Mar. 4, 2011, 6 pgs.
Australian Application Serial No. 2008243229, First Examiner Report mailed Apr. 13, 2010, 2 pgs.
Australian Application Serial No. 2008243229, Response filed May 13, 2011 to Office Action mailed Apr. 13, 2010, 15 pgs.
Australian Application Serial No. 2011253682, Response filed Jul. 17, 2013 to Office Action mailed Sep. 27, 2012, 19 pgs.
Canadian Application Serial No. 2,464,900, Office Action mailed Sep. 29, 2009, 3 pgs.
Canadian Application Serial No. 2,539,585, Office Action mailed Aug. 31, 2010, 2 pgs.
Canadian Application Serial No. 2,539,585, Office Action mailed Sep. 19, 2012, 2 pgs.

(56) References Cited

OTHER PUBLICATIONS

Canadian Application Serial No. 2,546,681, Office Action mailed Feb. 25, 2011, 3 pgs.
Canadian Application Serial No. 2,546,721, Office Action mailed Feb. 25, 2011, 3 pgs.
Canadian Application Serial No. 2,551,685, Office Action mailed Jan. 17, 2011, 3 pgs.
Canadian Application Serial No. 2,554,022, Office Action mailed Jun. 22, 2011, 3 pgs.
Canadian Application Serial No. 2,554,022, Office Action mailed Aug. 31, 2010, 2 pgs.
Canadian Application Serial No. 2,558,317, Office Action mailed Aug. 31, 2010, 2 pgs.
Canadian Application Serial No. 2,558,317, Office Action mailed Sep. 28, 2011, 3 pgs.
Canadian Application Serial No. 2,626,403, Response filed Feb. 12, 2014 to Office Action mailed Apr. 2, 2013, 20 pgs.
Chinese Application Serial No. 02823581.9, Office Action mailed Mar. 1, 2006, 7 pgs.
Chinese Application Serial No. 02823581.9, Office Action mailed Apr. 18, 2008, (W/ English Translation), 6 pgs.
Chinese Application Serial No. 02823581.9, Office Action mailed Aug. 8, 2007, 4 pgs.
Chinese Application Serial No. 02823581.9, Office Action mailed Nov. 17, 2006, 7 pgs.
Chinese Application Serial No. 02823581.9, Response filed Jan. 31, 2007 to Office Action mailed Nov. 17, 2006, 8 pgs.
Chinese Application Serial No. 02823581.9, Response filed Apr. 7, 2006 to Office Action mailed Mar. 1, 2006, 4 pgs.
Chinese Application Serial No. 02823581.9, Response filed May 19, 2008 to Office Action mailed Apr. 18, 2008, (W/ English Translation), 38 pgs.
Chinese Application Serial No. 02823581.9, Response filed Dec. 3, 2007 to Office Action mailed Aug. 8, 2007, 6 pgs.
Chinese Application Serial No. 200480027649.7, Office Action mailed Jun. 23, 2008, w/English translation, 5 pgs.
Chinese Application Serial No. 200480027649.7, Office Action mailed Sep. 4, 2009, w/English translation, 18 pgs.
Chinese Application Serial No. 200480027649.7, Office Action mailed Dec. 24, 2010, w/English translation, 6 pgs.
Chinese Application Serial No. 200480027649.7, Response filed Jan. 19, 2010 to Office Action mailed Sep. 4, 2009, 5 pgs.
Chinese Application Serial No. 200480027649.7, Response filed Mar. 8, 2011 to Office Action mailed Dec. 24, 2010, w/English translation, 7 pgs.
Chinese Application Serial No. 200480031226.2, Office Action mailed Jan. 23, 2009, w/English translation, 9 pgs.
Chinese Application Serial No. 200480031226.2, Office Action mailed Apr. 27, 2010, (W/ English Translation), 7 pgs.
Chinese Application Serial No. 200480031226.2, Office Action mailed Dec. 21, 2010, (W/ English Translation), 10 pgs.
Chinese Application Serial No. 200480031226.2, Response filed Feb. 25, 2011 to Office Action mailed Dec. 21, 2010, (W/ English Translation), 18 pgs.
Chinese Application Serial No. 200480031226.2, Response filed May 22, 2009 to Office Action mailed Jan. 23, 2009, 5 pgs.
Chinese Application Serial No. 200480031226.2, Response filed Jul. 12, 2010 to Office Action mailed Apr. 27, 2010, 5 pgs.
Chinese Application Serial No. 200580002026.9, Office Action mailed Jun. 19, 2009, (W/ English Translation), 12 pgs.
Chinese Application Serial No. 200580002026.9, Response filed Jan. 4, 2010 to Office Action mailed Jun. 19, 2009, 10 pgs.
Chinese Application Serial No. 200580006169.7, Office Action mailed Mar. 1, 2010, w/English translation, 12 pgs.
Chinese Application Serial No. 200580006169.7, Response filed Jul. 14, 2010 to Office Action mailed Mar. 1, 2010, w/English translation, 32 pgs.
Chinese Application Serial No. 200580009570.6, Office Action mailed May 9, 2008, (W/ English Translation), 2 pgs.
Chinese Application Serial No. 200580009570.6, Response filed Nov. 21, 2008 to Office Action mailed May 9, 2008, 7 pgs.
Chinese Application Serial No. 200680034052.4, Office Action mailed May 11, 2010, w/English translation, 7 pgs.
Chinese Application Serial No. 200680034052.4, Office Action mailed Aug. 14, 2009, w/English translation, 13 pgs.
Chinese Application Serial No. 200680034052.4, Response filed Mar. 1, 2010 to Office Action mailed Aug. 14, 2009, 4 pgs.
Chinese Application Serial No. 200680034052.4, Response filed Sep. 26, 2010 to Office Action mailed May 11, 2010, 5 pgs.
Chinese Application Serial No. 200680038882.4, Office Action mailed May 11, 2010, (W/ English Translation), 18 pgs.
Chinese Application Serial No. 200680046854.7, Office Action mailed Apr. 14, 2010, (W/ English Translation), 18 pgs.
Chinese Application Serial No. 200680046854.7, Response filed Sep. 26, 2010 to Office Action mailed Apr. 14, 2010, 10 pgs.
Chinese Application Serial No. 200680047552.1, Office Action mailed Jun. 4, 2010, (W/ English Translation), 7 pgs.
Chinese Application Serial No. 200680047552.1, Response filed Dec. 20, 2010 to Office Action mailed Jun. 4, 2010, 10 pgs.
Chinese Application Serial No. 200810210922.X, Office Action mailed Jan. 19, 2012, (W/ English Translation), 6 pgs.
Chinese Application Serial No. 200810210922.X, Office Action mailed Apr. 2, 2010, (W/ English Translation), 4 pgs.
Chinese Application Serial No. 200810210922.X, Office Action mailed Aug. 23, 2011, 6 pgs.
Chinese Application Serial No. 200810210922.X, Response filed Jun. 1, 2012 to Office Action mailed Jan. 19, 2012, 5 pgs.
Chinese Application Serial No. 200810210922.X, Response filed Aug. 12, 2010 to Office Action mailed Apr. 2, 2010, 10 pgs.
Chinese Application Serial No. 200910139527.1, Office Action mailed Jul. 12, 2010, w/English translation, 9 pgs.
Chinese Application Serial No. 200910139527.1, Response filed Nov. 28, 2011 to Office Action mailed Jul. 12, 2010, 9 pgs.
European Application Serial No. 02789196.9, European Search Report mailed Aug. 14, 2009, 5 pgs.
European Application Serial No. 02789196.9, Office Action mailed Feb. 6, 2012, 4 pgs.
European Application Serial No. 02789196.9, Office Action mailed Mar. 7, 2012, 3 pgs.
European Application Serial No. 02789196.9, Office Action mailed Apr. 19, 2010, 4 pgs.
European Application Serial No. 02789196.9, Office Action mailed Jul. 14, 2011, 3 pgs.
European Application Serial No. 02789196.9, Response filed Jan. 18, 2012 to Office Action mailed Jul. 14, 2011, 19 pgs.
European Application Serial No. 02789196.9, Response filed Feb. 16, 2012 to Office Action mailed Feb. 6, 2012, 9 pgs.
European Application Serial No. 02789196.9, Response filed Apr. 5, 2012 to Office Action mailed Mar. 7, 2012, 5 pgs.
European Application Serial No. 02789196.9, Response filed Oct. 25, 2010 to Office Action mailed Apr. 19, 2010, 16 pgs.
European Application Serial No. 04788653.6, Office Action mailed May 19, 2006, 2 pgs.
European Application Serial No. 05704902.5, European Search Report mailed Aug. 29, 2011, 3 pgs.
European Application Serial No. 05713941.2, Office Action mailed Dec. 13, 2007, 2 pgs.
European Application Serial No. 06802573.3, Extended European Search Report mailed Feb. 15, 2012, 6 pgs.
European Application Serial No. 06802573.3, Office Action mailed Mar. 5, 2012, 1 pg.
European Application Serial No. 06802573.3, Office Action mailed May 28, 2008, 2 pgs.
European Application Serial No. 06802573.3, Response filed Sep. 3, 2012 to Office Action mailed Mar. 5, 2012, 15 pgs.
European Application Serial No. 06802578.2, European Search Report mailed Mar. 7, 2013, 10 pgs.
European Application Serial No. 06802580.8, Extended European Search Report mailed Sep. 24, 2013, 8 pgs.
European Application Serial No. 06802580.8, Office Action mailed Feb. 25, 2013, 3 pgs.

(56) References Cited

OTHER PUBLICATIONS

European Application Serial No. 09075319.5, Extended European Search Report mailed Oct. 14, 2009, 6 pgs.
European Application Serial No. 09075319.5, Office Action mailed Jan. 14, 2010, 1 pgs.
European Application Serial No. 09075319.5, Office Action mailed Oct. 14, 2010, 4 pgs.
European Application Serial No. 09820886.1, Office Action mailed Jun. 7, 2011, 2 pgs.
European Application Serial No. 09820886.1, Response filed Dec. 8, 2011 to Office Action mailed Jun. 7, 2011, 3 pgs.
European Application Serial No. 09820891.1, Office Action mailed Jun. 7, 2011, 2 pgs.
European Application Serial No. 09820891.1, Response filed Dec. 8, 2011 to Office Action mailed Jun. 7, 2011, 2 pgs.
European Application Serial No. 09075319.5, Response filed Feb. 21, 2011 to Office Action mailed Oct. 14, 2010, 5 pgs.
European Application Serial No. 09075319.5, Response filed Jul. 20, 2010 to Office Action mailed Jan. 14, 2010, 13 pgs.
German Application Serial No. 10297483.7, Office Action mailed Jan. 9, 2006, 4 pgs.
German Application Serial No. 10297483.7, Office Action mailed Jul. 8, 2006, 2 pgs.
German Application Serial No. 10297483.7, Office Action mailed and Response filed Oct. 30, 2006, 8 pgs.
German Application Serial No. 10297483.7, Response filed Jul. 7, 2006 to Office Action mailed Jan. 9, 2006, 14 pgs.
German Application Serial No. 10297483.7, Response filed Oct. 26, 2006 to Office Action mailed Jul. 8, 2006, 3 pgs.
Great Britain Application Serial No. 0411107.6, Office Action mailed Feb. 28, 2005, 3 pgs.
Great Britain Application Serial No. 0411107.6, Office Action mailed Sep. 29, 2005, 1 pg.
Great Britain Application Serial No. 0411107.6, Response filed Aug. 23, 2005 to Office Action mailed Feb. 28, 2005, 3 pgs.
Great Britain Application Serial No. 0411107.6, Response filed Oct. 31, 2005 to Office Action mailed Sep. 29, 2005, 4 pgs.
Great Britain Application Serial No. 0522152.8, Office Action mailed Dec. 5, 2005, 5 pgs.
Great Britain Application Serial No. 0522152.8, Response filed Apr. 26, 2006 to Office Action mailed Dec. 5, 2005, 48 pgs.
International Application Serial No. PCT/US2002/032753, International Preliminary Examination Report mailed Aug. 16, 2004, 3 pgs.
International Application Serial No. PCT/US2002/032753, International Search Report mailed Mar. 6, 2003, 1 pg.
International Application Serial No. PCT/US2004/027589, International Preliminary Report on Patentability mailed Apr. 6, 2005, 4 pgs.
International Application Serial No. PCT/US2004/027589, International Search Report mailed Apr. 6, 2005, 1 pg.
International Application Serial No. PCT/US2004/027589, Written Opinion mailed Apr. 6, 2005, 3 pgs.
International Application Serial No. PCT/US2004/027590, International Preliminary Examination Report mailed Feb. 16, 2006, 3 pgs.
International Application Serial No. PCT/US2004/027590, International Search Report mailed Jan. 12, 2005, 1 pg.
International Application Serial No. PCT/US2004/027590, Written Opinion mailed Jan. 12, 2005, 3 pgs.
International Application Serial No. PCT/US2005/00059, International Preliminary Report on Patentability mailed May 18, 2007, 8 pgs.
International Application Serial No. PCT/US2005/00059, International Search Report mailed Jan. 5, 2007, 3 pgs.
International Application Serial No. PCT/US2005/00059, Written Opinion mailed Jan. 5, 2007, 8 pgs.
International Application Serial No. PCT/US2005/005453, International Preliminary Examination Report mailed Mar. 13, 2006, 3 pgs.
International Application Serial No. PCT/US2005/005453, International Preliminary Report on Patentability mailed Feb. 16, 2006, 3 pgs.
International Application Serial No. PCT/US2005/005453, International Search Report mailed Aug. 30, 2005, 1 pg.
International Application Serial No. PCT/US2005/005453, International Written Opinion mailed Aug. 30, 2005, 3 pgs.
International Application Serial No. PCT/US2005/005453, Written Opinion mailed Aug. 30, 2005, 3 pgs.
International Application Serial No. PCT/US2006/033747, International Preliminary Report on Patentability mailed Mar. 1, 2011, 4 pgs.
International Application Serial No. PCT/US2009/005604, International Preliminary Report on Patentability mailed Jan. 13, 2011, 10 pgs.
International Application Serial No. PCT/US2009/005607, International Preliminary Report on Patentability mailed Jan. 9, 2011, 9 pgs.
International Application Serial No. PCT/US2009/005607, International Search Report mailed Dec. 11, 2009, 2 pgs.
International Application Serial No. PCT/US2009/005607, Written Opinion mailed Dec. 11, 2009, 6 pgs.
International Application Serial No. PCT/US2009/005608, International Preliminary Report on Patentability mailed Jan. 14, 2011, 7 pgs.
International Application Serial No. PCT/US2009/005608, International Search Report mailed Dec. 10, 2009, 2 pgs.
International Application Serial No. PCT/US2009/005608, Written Opinion mailed Dec. 10, 2009, 4 pgs.
International Application Serial No. PCT/US2009/005609, International Preliminary Report on Patentability mailed Jan. 9, 2011, 9 pgs.
Japanese Application Serial No. 2003-546789, Office Action mailed Feb. 26, 2009, w/English translation, 7 pgs.
Japanese Application Serial No. 2003-546789, Office Action mailed Jun. 17, 2008, w/English translation, 6 pgs.
Japanese Application Serial No. 2003-546789, Office Action mailed Oct. 7, 2009, 3 pgs.
Japanese Application Serial No. 2003-546789, Response filed May 21, 2009 to Office Action mailed Feb. 26, 2009, 6 pgs.
Japanese Application Serial No. 2003-546789, Response filed Dec. 11, 2008 to Office Action mailed Jun. 17, 2008, w/English translation, 9 pgs.
Japanese Application Serial No. 2006-528036, Office Action mailed Jan. 19, 2010, 3 pgs.
Japanese Application Serial No. 2006-528036, Office Action mailed Feb. 26, 2009, w/English translation, 5 pgs.
Japanese Application Serial No. 2006-528036, Office Action mailed Jun. 23, 2008, w/English translation, 5 pgs.
Japanese Application Serial No. 2006-528036, Response filed Dec. 25, 2008 to Office Action mailed Jun. 23, 2008, w/English translation, 9 pgs.
Japanese Application Serial No. 2006-536616, Office Action mailed Jun. 23, 2008, (W/ English Translation), 8 pgs.
Japanese Application Serial No. 2006-536616, Response filed Dec. 19, 2008 to Office Action mailed Jun. 23, 2008, (W/ English Translation), 9 pgs.
Japanese Application Serial No. 2006-536617, Office Action mailed Jun. 17, 2008, (W/ English Translation), 3 pgs.
Japanese Application Serial No. 2006-536617, Response filed May 12, 2009 to Office Action mailed Jun. 17, 2008, (W/ English Translation), 19 pgs.
Japanese Application Serial No. 2006-547608, Office Action mailed Jun. 23, 2008, (W/ English Translation), 5 pgs.
Japanese Application Serial No. 2006-547608, Respone filed Dec. 19, 2008 to Office Action mailed Jun. 23, 2008, (W/ English Translation), 10 pgs.
Japanese Application Serial No. 2007500928, Office Action mailed Jul. 1, 2010, w/English translation, 10 pgs.
Japanese Application Serial No. 2007504965, Office Action mailed Mar. 7, 2012, w/English translation, 4 pgs.
Japanese Application Serial No. 2007504965, Office Action mailed Jun. 14, 2011, w/English translation, 4 pgs.
Japanese Application Serial No. 2007504965, Office Action mailed Sep. 14, 2010, English translation, 1 pg.
Japanese Application Serial No. 2007504965, Response filed Mar. 11, 2011 to Office Action mailed Sep. 14, 2010, 8 pgs.
Japanese Application Serial No. 2008-306790, Office Action mailed May 31, 2011, 1 pg.

(56) References Cited

OTHER PUBLICATIONS

Japanese Application Serial No. 2008-306790, Response filed Nov. 29, 2011 to Office Action mailed May 8, 2012, 2 pgs.
Japanese Application Serial No. 2008-306790, Response filed Nov. 29, 2011 to Office Action mailed May 31, 2011, (W/ English Translation), 12 pgs.
Japanese Application Serial No. 2008-316282, Office Action mailed May 16, 2011, 2 pgs.
Japanese Application Serial No. 2008-316296, Office Action mailed Feb. 28, 2011, 2 pgs.
Japanese Application Serial No. 2008-316296, Office Action mailed Jun. 22, 2010, 2 pgs.
Japanese Application Serial No. 2008-323279, Office Action mailed Sep. 30, 2010, 1 pg.
Japanese Application Serial No. 2008-323290, Office Action mailed Jun. 6, 2012, (W/ English Translation), 8 pgs.
Japanese Application Serial No. 2008-323290, Office Action mailed Jun. 8, 2011, (W/ English Translation), 8 pgs.
Japanese Application Serial No. 2008-323290, Response filed Dec. 7, 2011 to Office Action mailed Jun. 8, 2011, (W/ English Translation), 16 pgs.
Japanese Application Serial No. 2008-536574, Office Action mailed Mar. 11, 2010, (W/ English Translation), 4 pgs.
Japanese Application Serial No. 2008-536574, Office Action mailed Oct. 3, 2011, (W/ English Translation), 7 pgs.
Japanese Application Serial No. 2008-536575, Office Action mailed Jul. 7, 2011, (W/ English Translation), 5 pgs.
Japanese Application Serial No. 2008-536576, Office Action mailed Jul. 19, 2011, (W/ English Translation), 4 pgs.
Japanese Application Serial No. 2008-536577, Notice of Allowance mailed May 30, 2012, 3 pgs.
Japanese Application Serial No. 2008-536577, Office Action mailed Jul. 8, 2011, w/English translation, 4 pgs.
Japanese Application Serial No. 2008-536577, Response filed Jan. 6, 2012 to Office Action mailed Jul. 8, 2011, (W/ English Translation), 3 pgs.
U.S. Appl. No. 11/254,619, Advisory Action mailed Sep. 24, 2014, 3 pgs.
U.S. Appl. No. 11/254,619, Examiner Interview Summary mailed Sep. 18, 2014, 3 pgs.
U.S. Appl. No. 11/254,619, Final Office Action mailed Jun. 19, 2014, 17 pgs.
U.S. Appl. No. 11/254,619, Final Office Action mailed Jun. 30, 2010, 10 pgs.
U.S. Appl. No. 11/254,619, Final Office Action mailed Oct. 20, 2011, 11 pgs.
U.S. Appl. No. 11/254,619, Non Final Office Action mailed Feb. 3, 2011, 8 pgs.
U.S. Appl. No. 11/254,619, Non Final Office Action mailed Oct. 1, 2009, 5 pgs.
U.S. Appl. No. 11/254,619, Response filed May 6, 2014 to Non Final Office Action mailed Jan. 6, 2014, 10 pgs.
U.S. Appl. No. 11/254,619, Response filed Sep. 15, 2014 to Final Office Action mailed Jun. 19, 2014, 12 pgs.
U.S. Appl. No. 11/488,305, Final Office Action mailed Aug. 14, 2014, 11 pgs.
U.S. Appl. No. 11/488,305, Response filed Apr. 29, 2014 to Non Final Office Action mailed Jan. 29, 2014, 9 pgs.
U.S. Appl. No. 11/981,112, Examiner Interview Summary mailed Jul. 3, 2014, 3 pgs.
U.S. Appl. No. 11/981,112, Response filed Jun. 27, 2014 to Non Final Office Action mailed Feb. 28, 2014, 11 pgs.
U.S. Appl. No. 12/288,031, Advisory Action mailed Jul. 7, 2014, 4 pgs.
U.S. Appl. No. 12/288,031, Non Final Office Action mailed May 10, 2012, 7 pgs.
U.S. Appl. No. 12/288,031, Response filed Jun. 5, 2014 to Final Office Action mailed Mar. 12, 2014, 15 pgs.
U.S. Appl. No. 12/288,031, Response filed Sep. 10, 2014 to Advisory Action mailed Jul. 7, 2014, 16 pgs.
U.S. Appl. No. 12/288,034, Non Final Office Action mailed May 8, 2014, 8 pgs.
U.S. Appl. No. 12/288,034, Response filed Aug. 1, 2014 to Non Final Office Action mailed May 8, 2014, 11 pgs.
U.S. Appl. No. 12/315,015, Non Final Office Action mailed Aug. 4, 2014, 7 pgs.
U.S. Appl. No. 12/315,015, Response filed Jun. 17, 2014 to Final Office Action mailed Jan. 28, 2014, 7 pgs.
U.S. Appl. No. 12/942,232, Advisory Action mailed Aug. 7, 2014, 3 pgs.
U.S. Appl. No. 12/942,232, Final Office Action mailed May 22, 2014, 17 pgs.
U.S. Appl. No. 12/942,232, Response filed Jul. 21, 2014 to Final Office Action mailed May 22, 2014, 11 pgs.
U.S. Appl. No. 13/157,242, Notice of Allowance mailed May 9, 2014, 8 pgs.
U.S. Appl. No. 13/157,242, Notice of Allowance mailed Aug. 21, 2014, 8 pgs.
U.S. Appl. No. 14/210,683, Preliminary Amendment mailed Mar. 24, 2014, 7 pgs.
Australian Application Serial No. 2011224089, Response filed Mar. 21, 2014 to First Examiners Report mailed Mar. 27, 2013, 74 pgs.
European Application Serial No. 05713941.2, European Search Report mailed Apr. 10, 2014, 6 pgs.
European Application Serial No. 05713941.2, Examination Notification Art. 94(3) mailed Jun. 5, 2014, 7 pgs.
European Application Serial No. 05723408.0, Examination Notification Art. 94(3) mailed Jul. 10, 2014, 6 pgs.
European Application Serial No. 06802580.8, Response filed Apr. 17, 2014 to Extended European Search Report mailed Sep. 24, 2013, 2 pgs.
U.S. Appl. No. 14/595,928, filed Jan. 13, 2015, Endovascular Aneurysm Devices, Systems, and Methods.
U.S. Appl. No. 11/981,112, Final Office Action mailed Oct. 24, 2014, 7 pgs.
U.S. Appl. No. 11/981,112, Response filed Jan. 12, 2014 to Final Office Action mailed Oct. 24, 2014, 9 pgs.
U.S. Appl. No. 12/288,031, Non Final Office Action mailed Feb. 17, 2015, 17 pgs.
U.S. Appl. No. 12/288,031, Respnse filed May 18, 2015 to Non Final Office Action mailed Feb. 17, 2015, 20 pgs.
U.S. Appl. No. 12/288,034, Final Office Action mailed Dec. 1, 2014, 8 pgs.
U.S. Appl. No. 12/315,015, Examiner Interview Summary mailed Nov. 28, 2014, 3 pgs.
U.S. Appl. No. 12/315,015, Final Office Action mailed Dec. 5, 2014, 9 pgs.
U.S. Appl. No. 12/315,015, Non Final Office Action mailed Mar. 30, 2015, 10 pgs.
U.S. Appl. No. 12/315,015, Response filed Mar. 5, 2015 to Final Office Action mailed Dec. 5, 2014, 13 pgs.
U.S. Appl. No. 12/315,015, Response filed Nov. 4, 2014 to Non-Final Office Action mailed Aug. 4, 2014, 7 pgs.
U.S. Appl. No. 13/157,242, Notice of Allowance mailed Jan. 14, 2015, 8 pgs.
U.S. Appl. No. 14/230,469, Non Final Office Action mailed May 7, 2015, 8 pgs.
U.S. Appl. No. 14/595,928, Preliminary Amendment filed Jan. 14, 2015, 8 pgs.
Australian Application Serial No. 2004287355, European Search Report mailed Oct. 14, 2009, 6 pgs.
Canadian Application Serial No. 2,546,721, Office Action mailed Aug. 31, 2010, 2 pgs.
Canadian Application Serial No. 2,546,721, Response filed Aug. 1, 2012 to Office Action mailed Feb. 25, 2011, 9 pgs.
European Application Serial No. 04788653.6, European Search Report mailed Aug. 6, 2014, 3 pgs.
European Application Serial No. 04788653.6, Examination Notification Art. 94(3) mailed Mar. 3, 2015, 4 pgs.
European Application Serial No. 04788653.6, Response filed Oct. 21, 2014 to European Search Report mailed Aug. 6, 2014, 4 pgs.
European Application Serial No. 05713941.2, Response filed Dec. 22, 2014 to Examination Notification Art. 94(3) mailed Jun. 5, 2014, 15 pgs.
European Application Serial No. 05723408.0, Response filed Jan. 19, 2015 to Examination Notification Art. 94(3) mailed Jul. 10, 2014, 16 pgs.
European Application Serial No. 09820886.1, Extended European Search Report mailed Mar. 27, 2015, 8 pgs.

\* cited by examiner

ENDOVASCULAR ANEURYSM REPAIR SYSTEM

RELATED APPLICATION

This application is a divisional of U.S. application Ser. No. 11/166,411, filed on Jun. 24, 2005, which is a divisional of U.S. application Ser. No. 10/271,334, filed Oct. 15, 2002, which claims the benefit of U.S. Provisional Application No. 60/333,937, filed on Nov. 28, 2001. The contents of all these disclosures are incorporated herein in their entirety.

BACKGROUND OF THE INVENTION

The invention relates generally to the attachment of a vascular prosthesis to a native vessel, and in particular, to a method and system of devices for the repair of diseased and/or damaged sections of a vessel.

DESCRIPTION OF RELATED ART

The weakening of a vessel wall from damaged or diseased can lead to vessel dilatation and the formation of an aneurysm. Left untreated, an aneurysm can grow in size and will eventually rupture.

For example, aneurysms of the aorta primarily occur in abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic graft, made either in a straight of bifurcated configuration, is installed and then permanently attached and sealed to the ends of the native vessel by suture. The prosthetic grafts for these procedures are usually unsupported woven tubes and are typically made from polyester, ePTFE or other suitable materials. The grafts are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co morbidities.

Endovascular aneurysm repair has been introduced to overcome the problems associated with open surgical repair. The aneurysm is bridged with a vascular prosthesis, which is placed intraluminally. Typically these prosthetic grafts for aortic aneurysms are delivered collapsed on a catheter through the femoral artery. These grafts are usually designed with a fabric material attached to a metallic scaffolding (stent) structure, which expands or is expanded to contact the internal diameter of the vessel. Unlike open surgical aneurysm repair, intraluminally deployed grafts are not sutured to the native vessel, but rely on either barbs extending from the stent, which penetrate into the native vessel during deployment, or the radial expansion force of the stent itself is utilized to hold the graft in position. These graft attachment means do not provide the same level of attachment when compared to suture and can damage the native vessel upon deployment.

Accordingly, there is a need for an endovascular aneurysm repair system that first provides a prosthetic graft, which can adapt to changes in aneurysm morphology and be deployed without damaging the native vessel and second, a separate endovascular fastening system that provides permanent graft attachment to the vessel wall.

SUMMARY OF THE INVENTION

The methods and apparatus for implanting radially expandable prostheses is the body lumens are described. In particular, the present invention provides improved methods and systems for implanting vascular stents and stent-grafts into blood vessels, including both arterial and venous systems. In the exemplary embodiments, stent-grafts are placed in vasculature to reinforce aneurysms, particularly abdominal aortic aneurysms.

In the first aspect of the present invention, a radially expandable prosthesis is placed in a body lumen by first expanding at least one scaffold of the prosthesis at or near an implantation site within the body lumen, e.g., at or from vasculature on one side of an aneurysm. After expanding the scaffold of the prosthesis, a plurality of fasteners are introduced through the prosthesis in the region in the scaffold to anchor the scaffold in place. The scaffold may be elastic, typically comprised of a shape memory alloy elastic stainless steel, or the like. For elastic scaffolds, expanding typically comprises releasing the scaffolding from constraint to permit the scaffold to self-expand at the implantation site. The constraint may be radial constraint, i.e., placement of a tubular catheter, delivery sheath, or the like over the scaffold in order to maintain the scaffold in a radially reduced configuration. Expansion is then achieved by pulling back on the catheter sheath to permit the scaffold to return to its larger diameter configuration. Alternatively, the scaffold may be constrained in an axially elongated configuration, e.g., by attaching either end of the scaffold to an internal tube, rod, catheter or the like, to maintain the scaffold in the elongated, reduced diameter configuration. The scaffold may then be released from such axial constraint in order to permit self-expansion.

Alternatively, the scaffold may be formed from a malleable material, such as malleable stainless steel of other metals. Expansion may then comprise applying a radially expansive force within the scaffold to cause expansion, e.g., inflating a scaffold delivery catheter within the side of the scaffolding order to affect the expansion.

The vascular prosthesis may have a wide variety of conventional configurations. In the preferred placement of the vascular stent-graft, prosthesis would typically comprise a fabric other blood semi-impermeable flexible barrier which is supported by a scaffold, typically in the form of a stent. A stent can have any conventional stent configurations, such as zigzag, serpentine, expanding diamond, or combinations thereof. The stent structure may extend the entire length of the graft, and in some instances will be longer than the fabric components of the graft. Alternatively, the stent will cover only a small portion of the prosthesis, e.g., being present on at 1, 2, or 3 ends. The stent may have three or more ends when it is configured to treat bifurcated vascular regions, such as the treatment of abdominal aortic aneurysms when the stent graft extends into the iliac arteries. In certain instances, the stents may be spaced apart along the entire length, or at least a major portion of the entire length, of the stent-graft, where individual stent structures are not connected to each other directly, but rather connected to the fabric or other flexible component of the graft.

Introduction of the fasteners will typically be effected after the prosthesis has been initially placed. That is initial placement will be achieved by self-expansion or balloon expansion, after which the prosthesis is secured or anchored in place by the introduction of a plurality of individual fasteners, preferably helical fasteners which are rotated and "screwed into" the prosthesis and vessel wall. Fasteners may be placed through the fabric only, i.e., avoiding the scaffold structure. Alternately, the fasteners can be introduced into and through portions of the scaffold structure, optionally through receptacles or apertures which have been specially configured to receive the fasteners. In some cases, of course, fasteners will be introduced both through the fabric and through of over the scaffold structure.

In the exemplary embodiment, the fasteners are helical fasteners, which are introduced singly, i.e., one at a time, in a circumferentially spaced-apart pattern over an interior wall of the prosthesis. Usually, the fasteners will be introduced using a fastener applier which carries a single fastener. Fastener appliers which carry a single fastener can have a lower profile and may be more effective and less traumatic than fastener appliers which carry multiple fasteners. The present invention, however, does contemplate that in certain embodiments the fastener applier may carry multiple fasteners. Moreover, the fastener applier may simultaneously deploy multiple fasteners in the preferred circumferentially spaced-apart space pattern described above. Usually, from 2-12 fasteners will be applied at each end of the prosthesis to be anchored. The 2-12 fasteners will usually be applied in a single circumferentially space-apart row that may be applied in more than one row with individual fasteners being axially aligned or circumferentially staggered. In a preferred embodiment, the intraluminal fastener applier of the present invention comprises a guide component and an applier component. The guide component, for example, comprises a tubular body having a deflectable distal tip and, optionally, a stabilizer for holding the deflected tip against a location in the graft to which the fastener is to be applied. The applier component is insertable through a lumen of the guide component and carries at least a single helical or other fastener. A rotation driver is provided for rotating and advancing the helical fastener so that it penetrates the graft and underlying vessel wall to anchor the graft firmly in place.

BRIEF DESCRIPTION OF THE DRAWINGS

The invention will be understood from the following detailed description of preferred embodiments, taken in conjunction with the accompanying drawings, wherein.

DETAILED DESCRIPTION OF THE INVENTION

Figure 1:
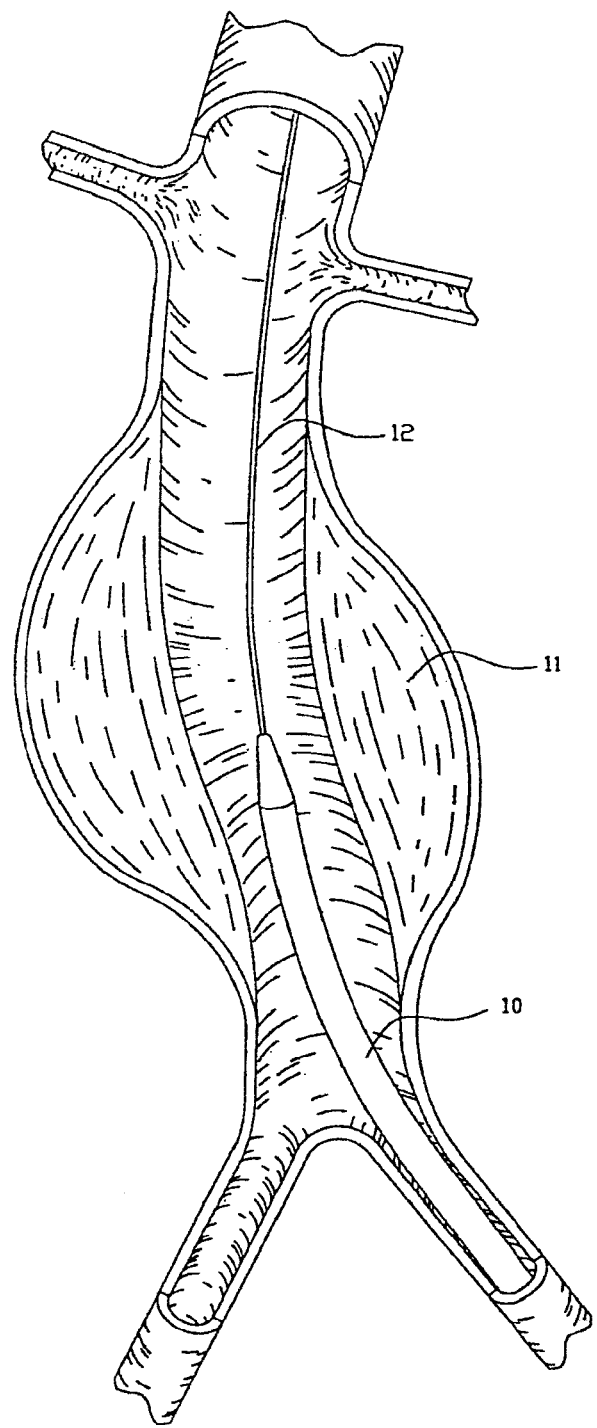
FIG. 1 is a perspective view of one embodiment of an endovascular graft delivery device shown positioned within an abdominal aortic aneurysm.
Figure 2:
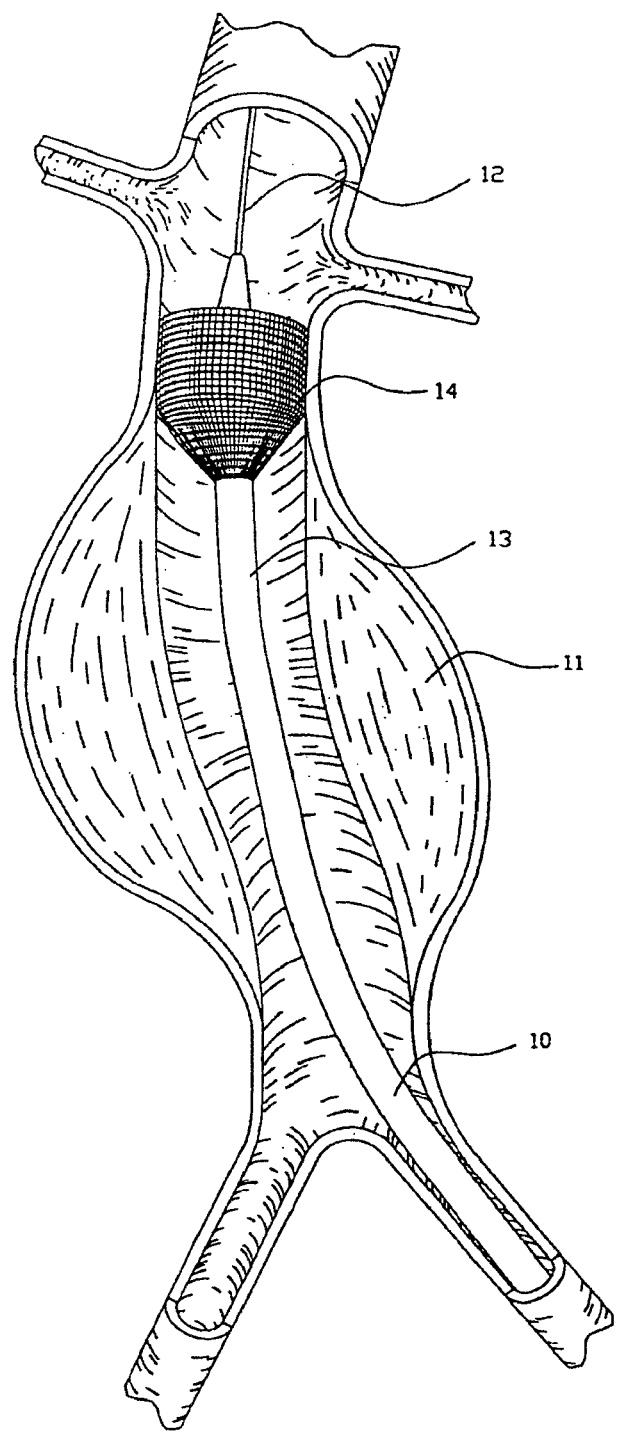
FIG. 2 is a perspective view of one embodiment the deployment of an endovascular graft within the aneurysm of FIG. 1.
Figure 3:
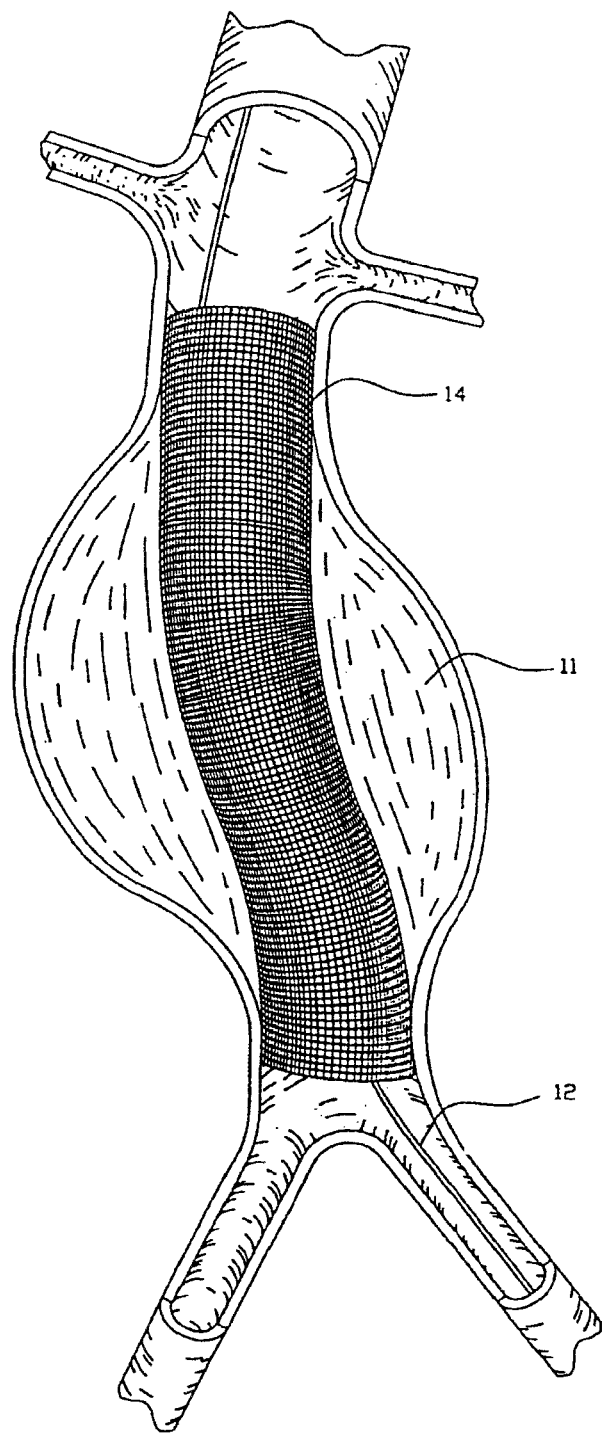
FIG. 3 is a perspective view of a fully deployed straight endovascular graft of FIG. 2.
Figure 4:
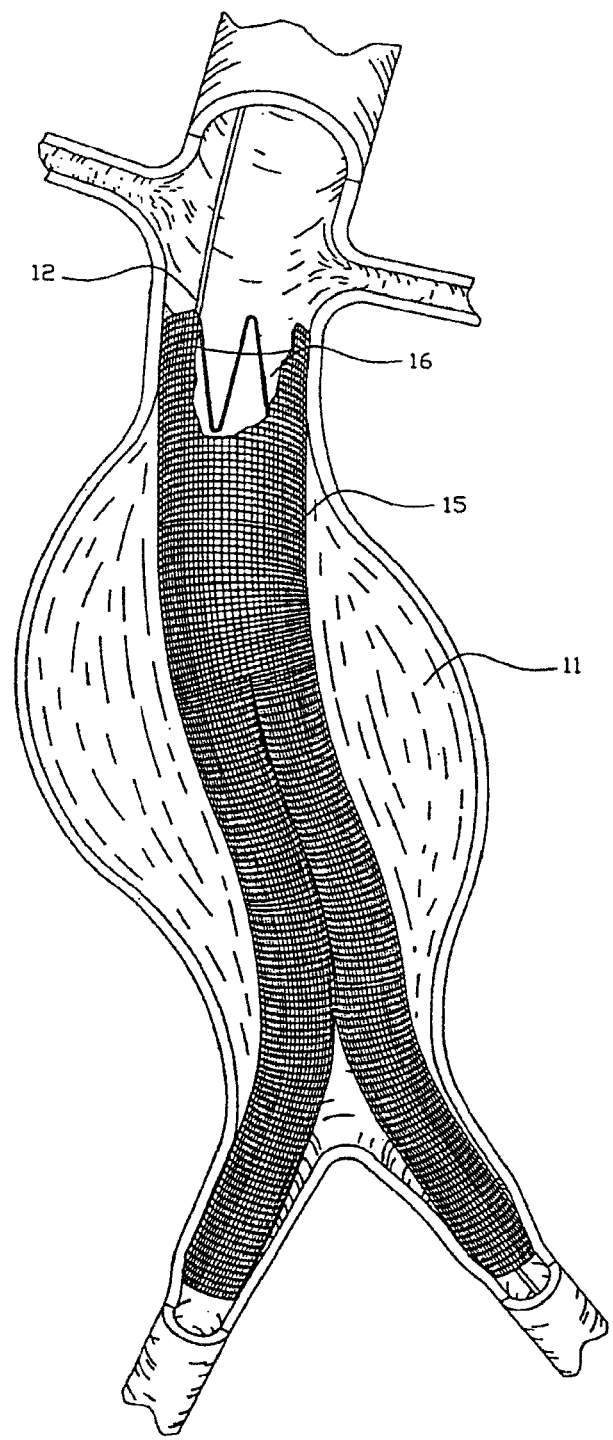
FIG. 4 is a perspective view of a fully deployed bifurcated endovascular graft broken away to show an anchoring scaffold at one end.
Figure 5:
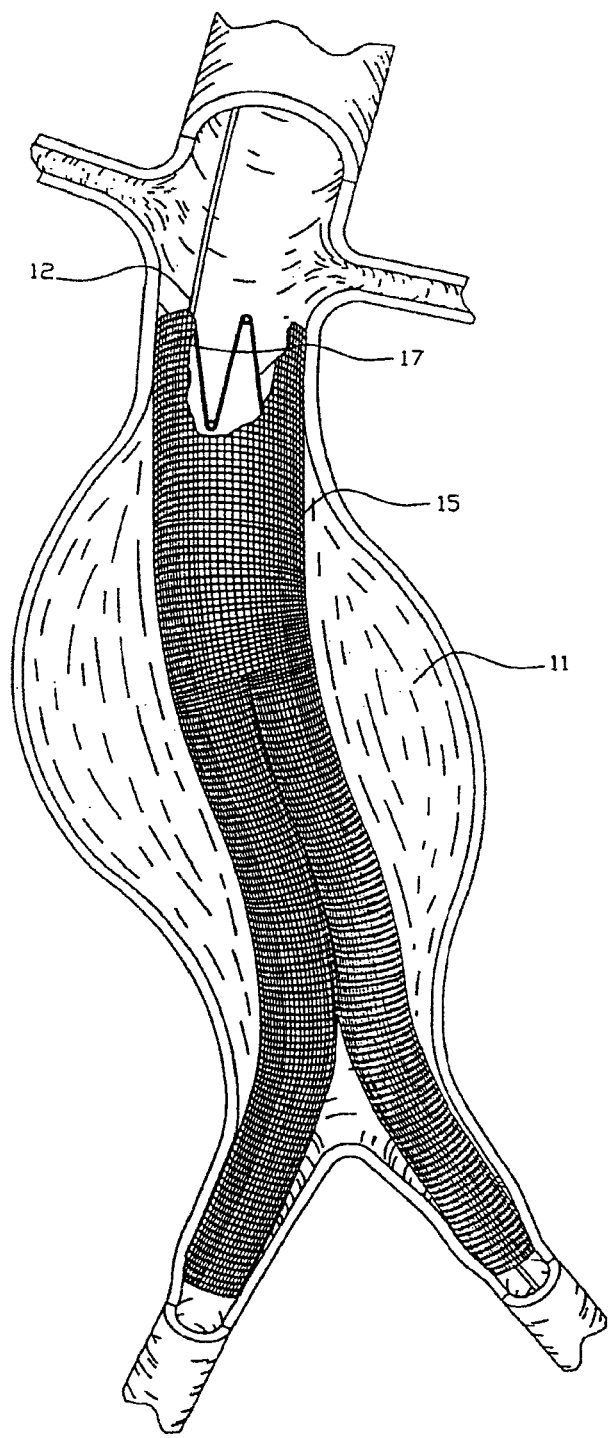
FIG. 5 is a perspective view similar to FIG. 5 showing an alternative scaffold structure.
Figure 6:
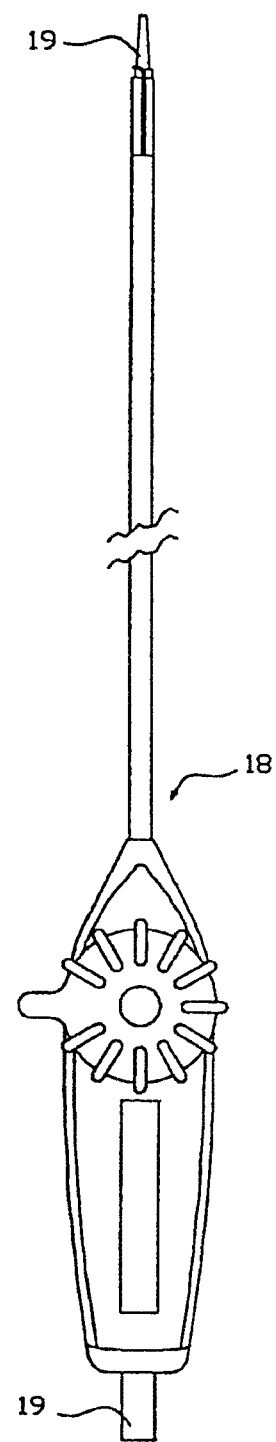
FIG. 6 is a perspective view showing one embodiment of a device for directing the fastener applier.
Figure 7:
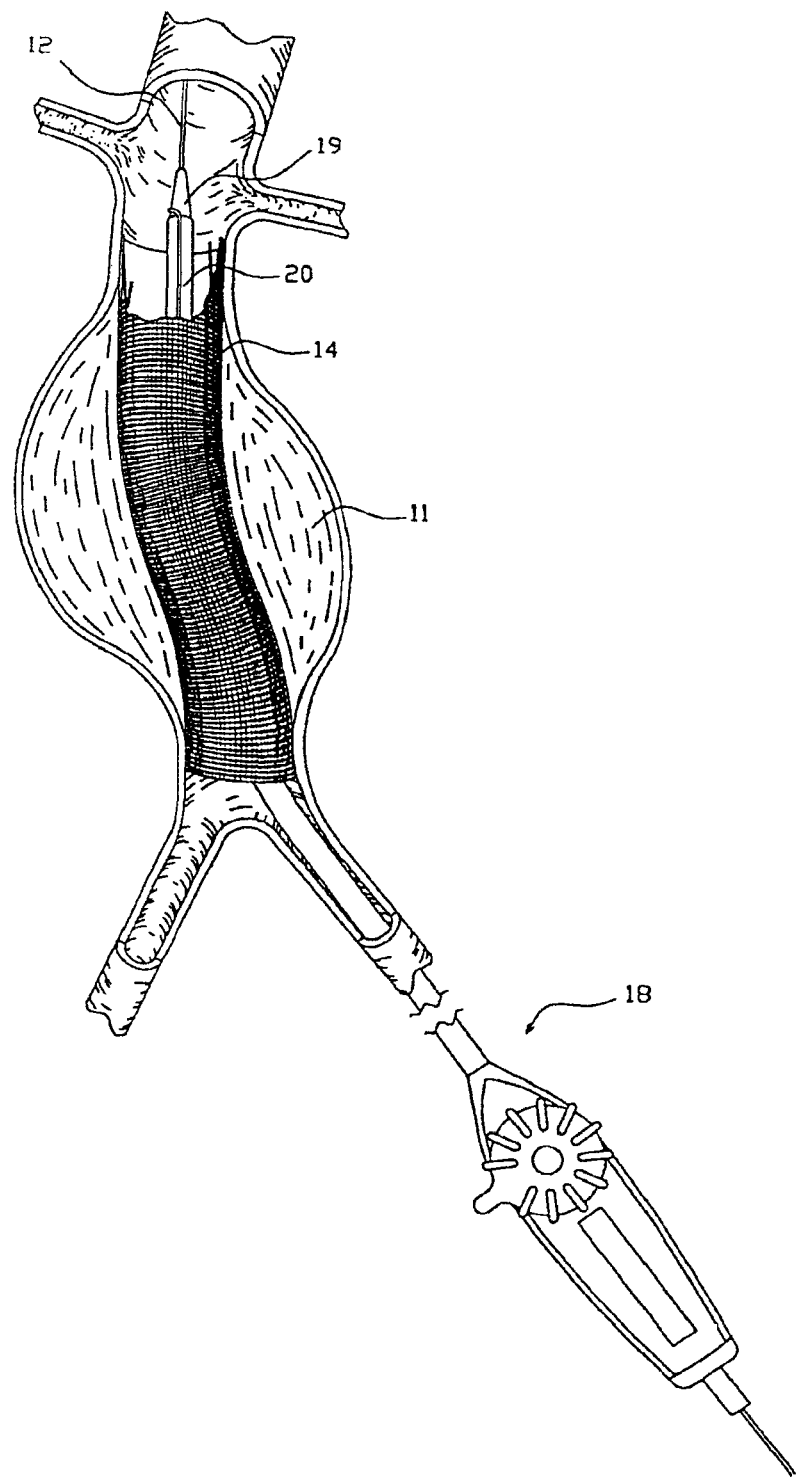
FIG. 7 is a perspective view showing the device of FIG. 6 upon insertion within the deployed endovascular graft of FIG. 3 with both the graft and scaffolding broken away.
Figure 8:
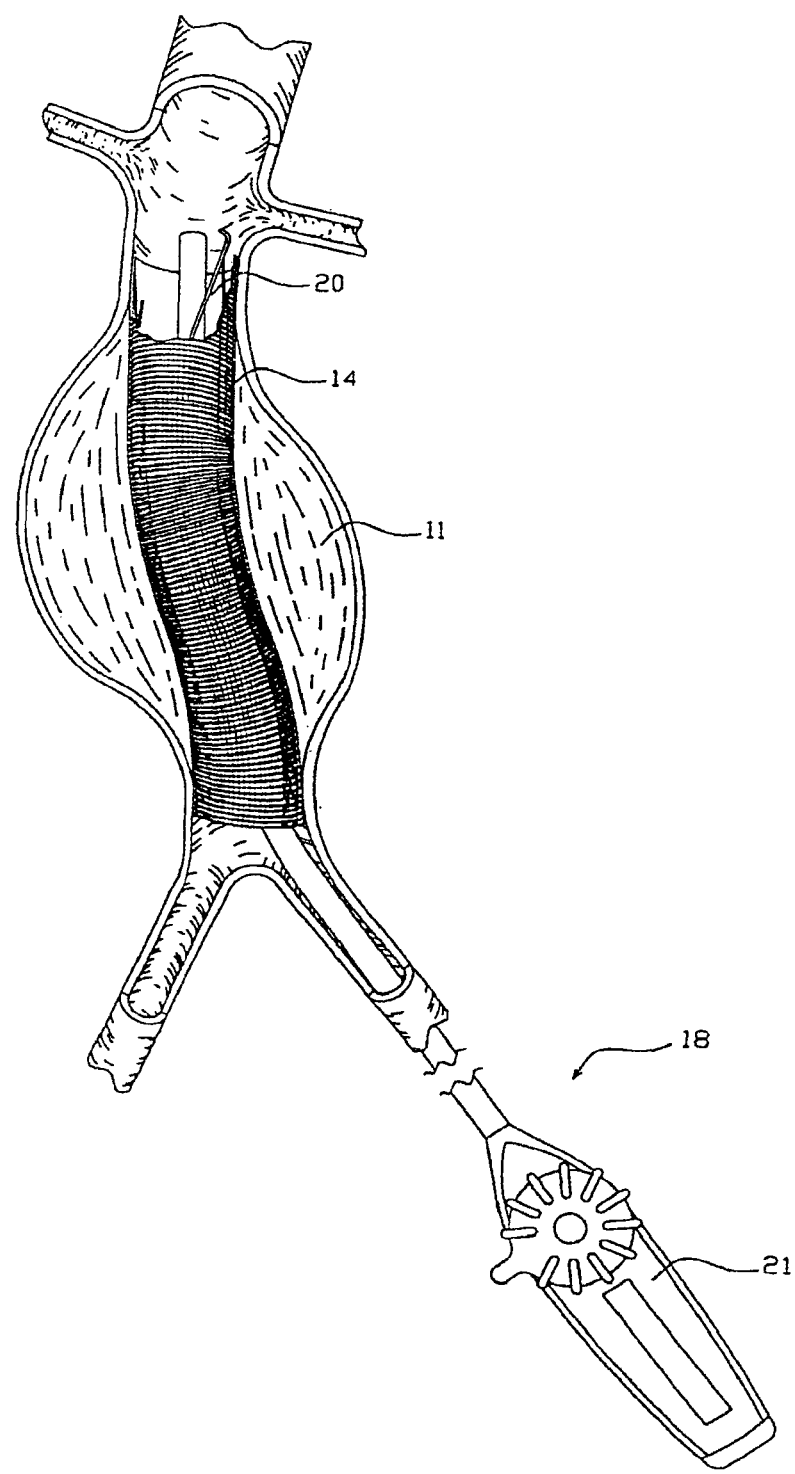
FIG. 8 is a perspective view of the device of FIG. 6 showing activation of one embodiment of a stabilizing device attached to the directing device.
Figure 9:
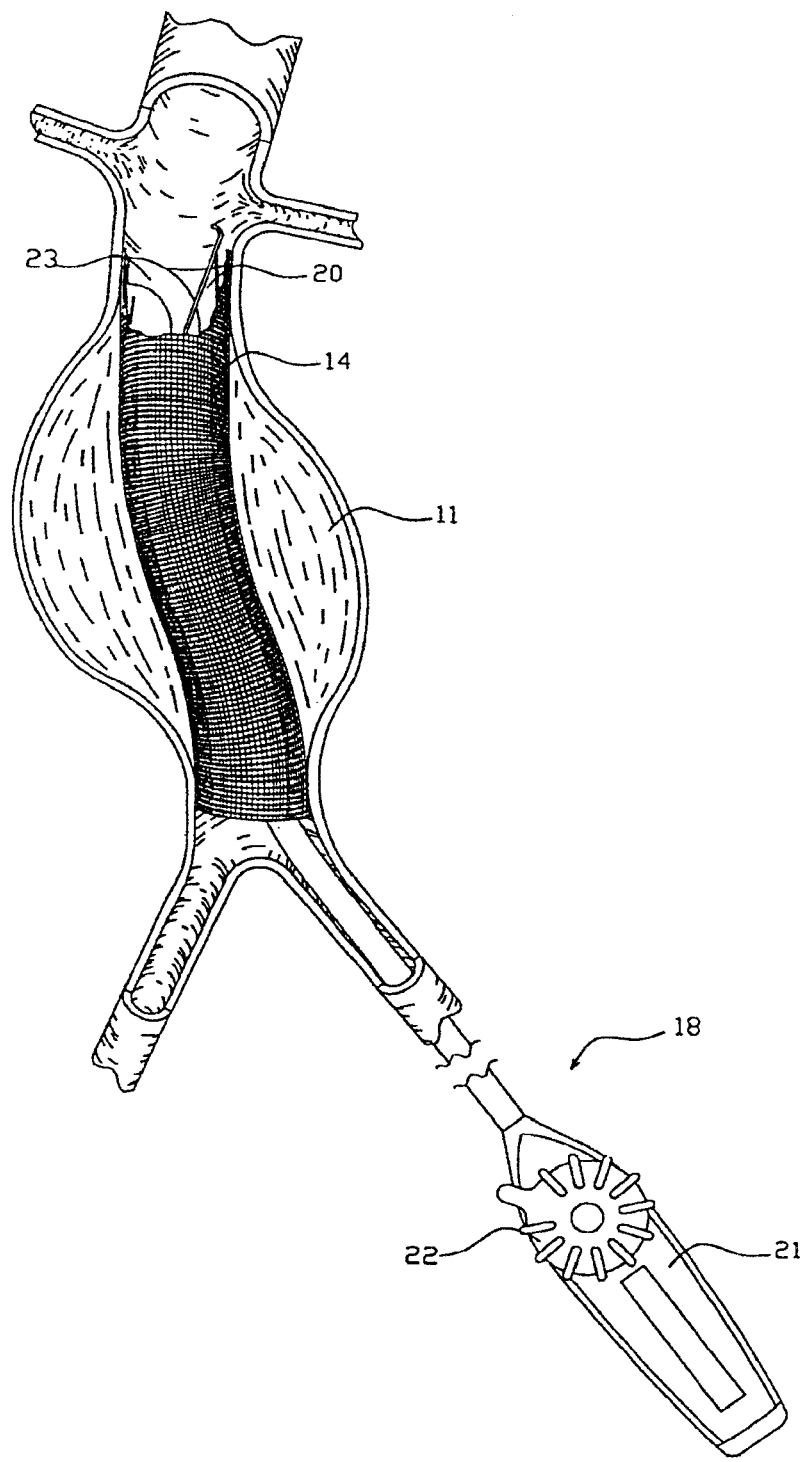
FIG. 9 is a perspective view of the control assembly in FIG. 8 articulating the directing device of FIG. 6.
Figure 10:
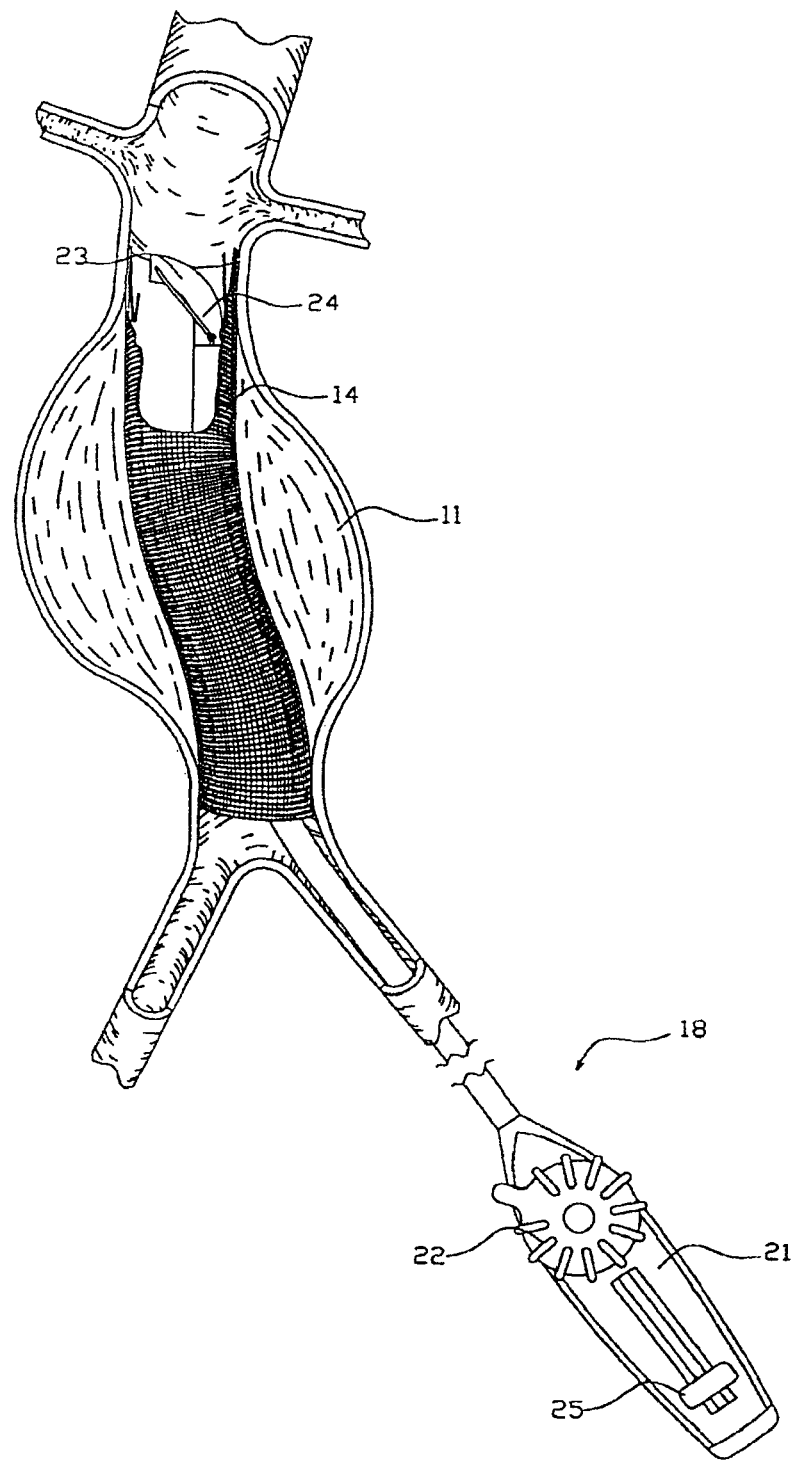
FIG. 10 is a perspective view of an alternative embodiment of the stabilization device of FIG. 8.
Figure 11:
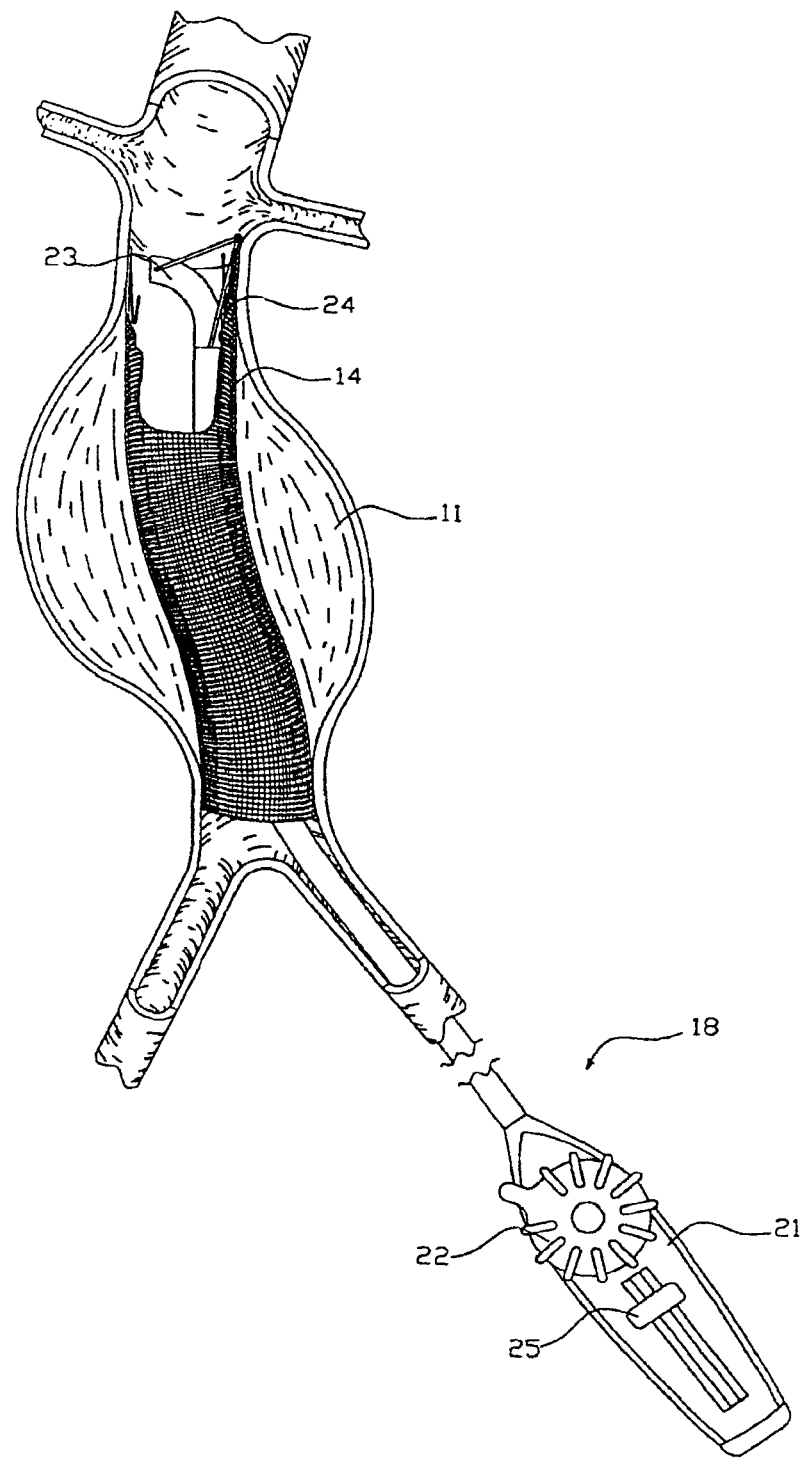
FIG. 11 is a perspective view showing the activation of the alternative stabilization device of FIG. 10.
Figure 12:
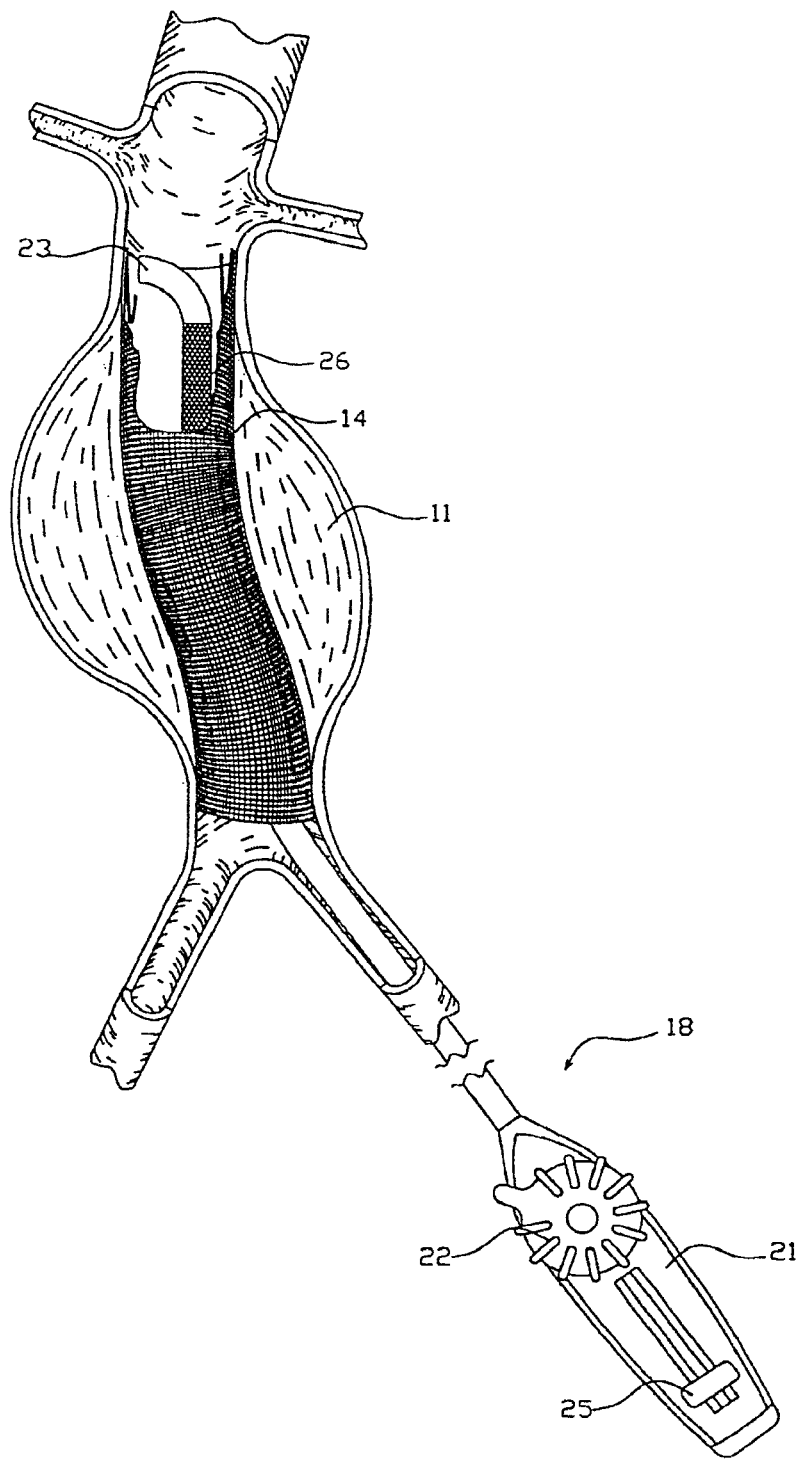
FIG. 12 is a perspective view showing another embodiment of the stabilization device of FIG. 8.
Figure 13:
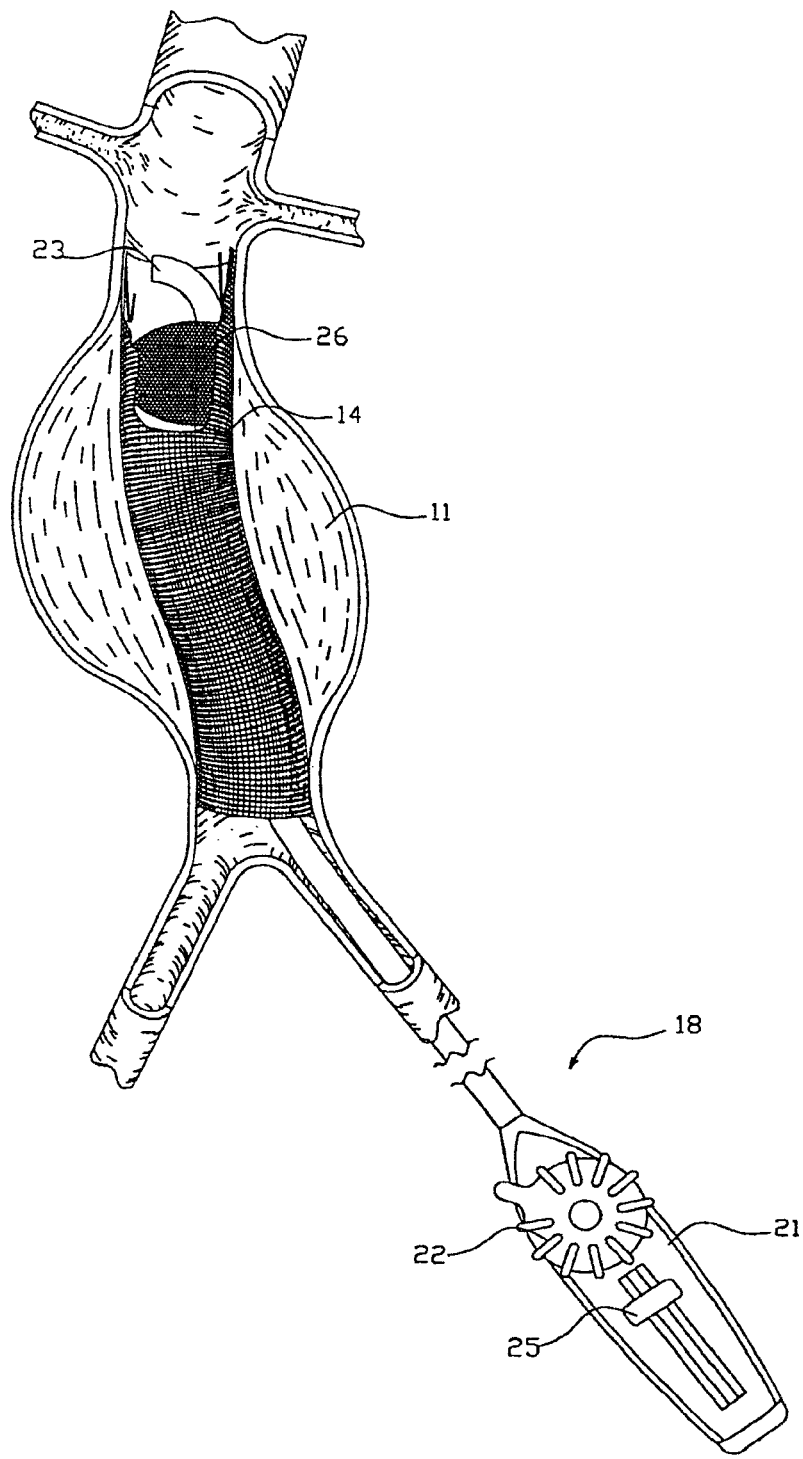
FIG. 13 is a perspective view showing activation of the stabilization device of FIG. 12.

FIG. 1 depicts an endovascular graft delivery catheter 10 being positioned within an abdominal aortic aneurysm 11 over a guidewire 12. FIG. 2 depicts the initial stage of graft deployment within a vessel. The delivery catheter 10 has a movable cover 13 over the graft. When the cover is pulled proximally the graft 14 expands to contact the internal walls of the vessel. It is contemplated that the graft could be self-expanding or utilize an expanding member such as a balloon or mechanical expander. The process of graft deployment is continued until the graft is fully deployed within the vessel. It is contemplated that the graft could be in either a straight or bifurcated form. FIG. 3 depicts a completely deployed straight graft 14 and FIG. 4 depicts a completely deployed bifurcated graft 15. The guidewire 11 used to deliver and position the graft remains within the vessel for access of the fastener attachment system. One embodiment of the graft scaffolding 16 (stent) is illustrated in the area broke away in FIG. 4. The stent is in the form of a simple zigzag pattern, however it is contemplated that the stent design could involve more complex patterns 17 as depicted in FIG. 5. Although only one stent structure within the graft is depicted, in FIGS. 4 and 5, it is contemplated that multiple independent stent structures could be incorporated into the graft. 1391 FIG. 6 depicts one embodiment of the directing device 18 with an obturator 19 positioned within the lumen of the directing device and extending past the distal of the tip of the directing device. The obturator has a lumen to allow for delivery over a guidewire. FIG. 7 depicts the directing device being positioned within the deployed endovascular graft over a Quidewire 12. The directing device has an incorporated stabilizing device 20 to aid in maintaining position of the directing device within the vessel. In one embodiment, the stabilizing device 20 is spring-loaded and is positioned for use when the obturator in the directing device is removed FIG. 8. The directing device is activated though a control assembly 21 as seen in FIG. 8. In one embodiment the control assembly 21 features a movable wheel or lever 22, which deflects the distal tip 23 of the directing device 18 to the desired location as seen in FIG. 9. It is contemplated that the control assembly for the directing device could be activated mechanically, electrically, hydraulically or pneumatically. The control assembly has a through lumen to allow for the passage of the obturator and fastener applier. FIG. 10 depicts another embodiment the stabilizing device as a movable strut assembly 24. The movable strut assembly is activated through a lever 25 on the control assembly FIG. 11. In both embodiments (FIGS. 7 and 10) the stabilizing device is distal to the end of the directing device. In another embodiment the stabilizing device could be in the form of an expandable member 26 adjacent to the distal tip of the directing device FIG. 12. In one embodiment, the expandable member 26 is shown activated through a lever 25 on the control assembly FIG. 13. However it also contemplated that this type of stabilizing device could also be inflatable. In all embodiments the stabilizing device could be use to stabilize the directing member either concentrically or eccentrically within the vessel.

In another embodiment of the invention a separate tubular device could be used in cooperation with the directing device and to access the vessel. This separate tubular device could incorporate the stabilizing devices used above with the directing device.

Figures 14, 14A:
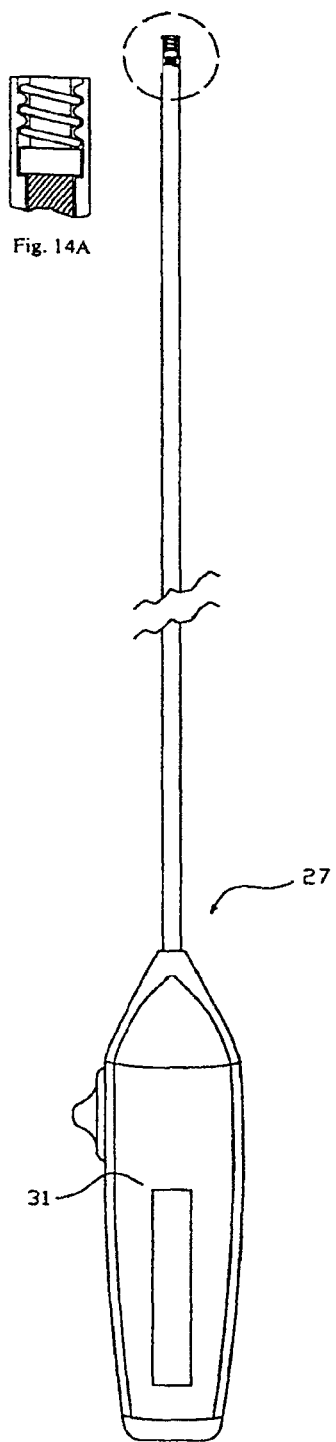
FIG. 14 is one embodiment of the fastener applier.
Figure 15:
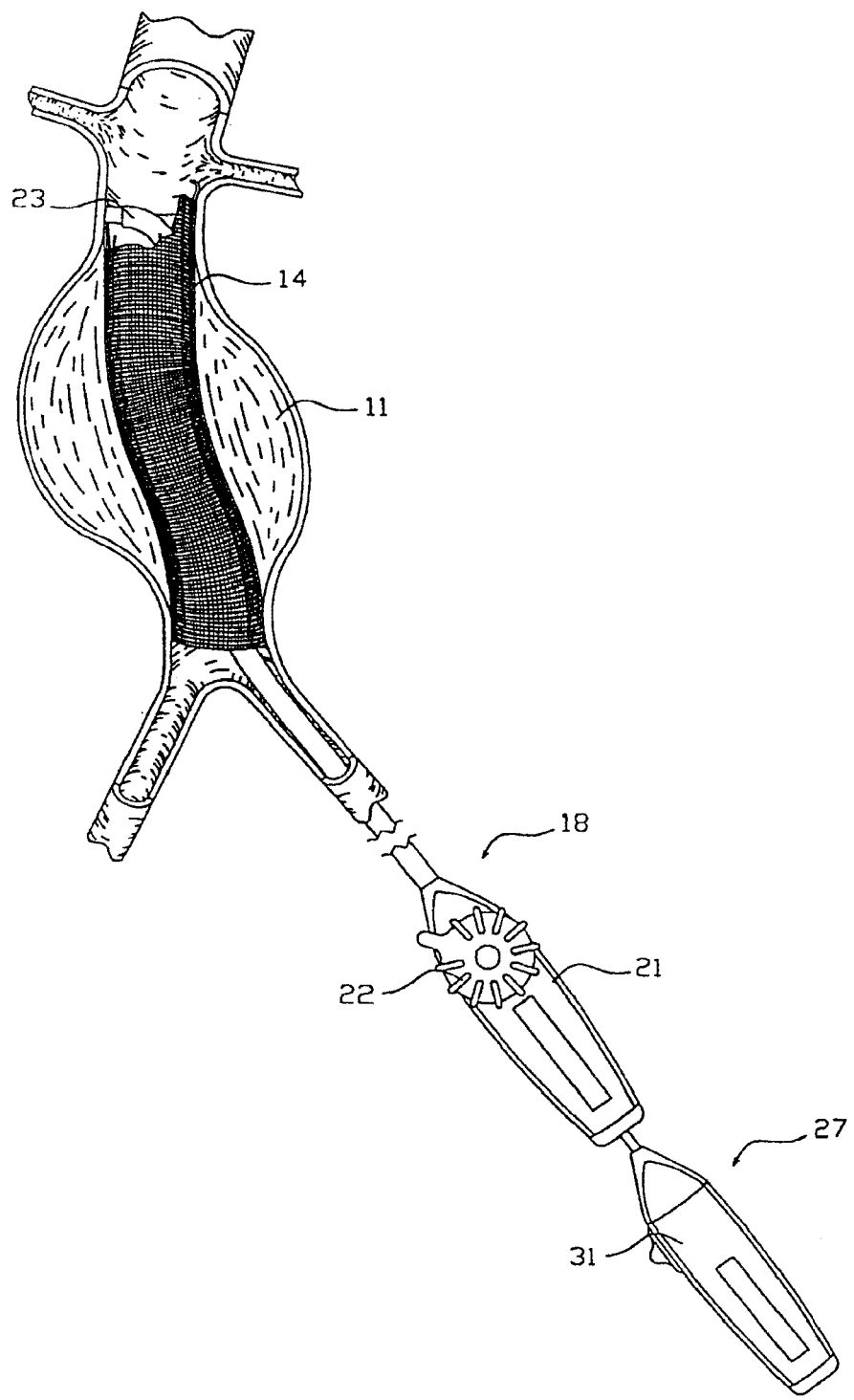
FIG. 15 is a perspective view of the fastener applier of FIG. 14 being positioned within directing device of FIG. 6.

FIG. 14 depicts one embodiment of the fastener applier 27. FIG. 14A is a detail view of the distal end of the fastener applier. FIG. 15 depicts the fastener applier being positioned through the lumen of the directing device to the site where a fastener will be installed.

Figure 16:
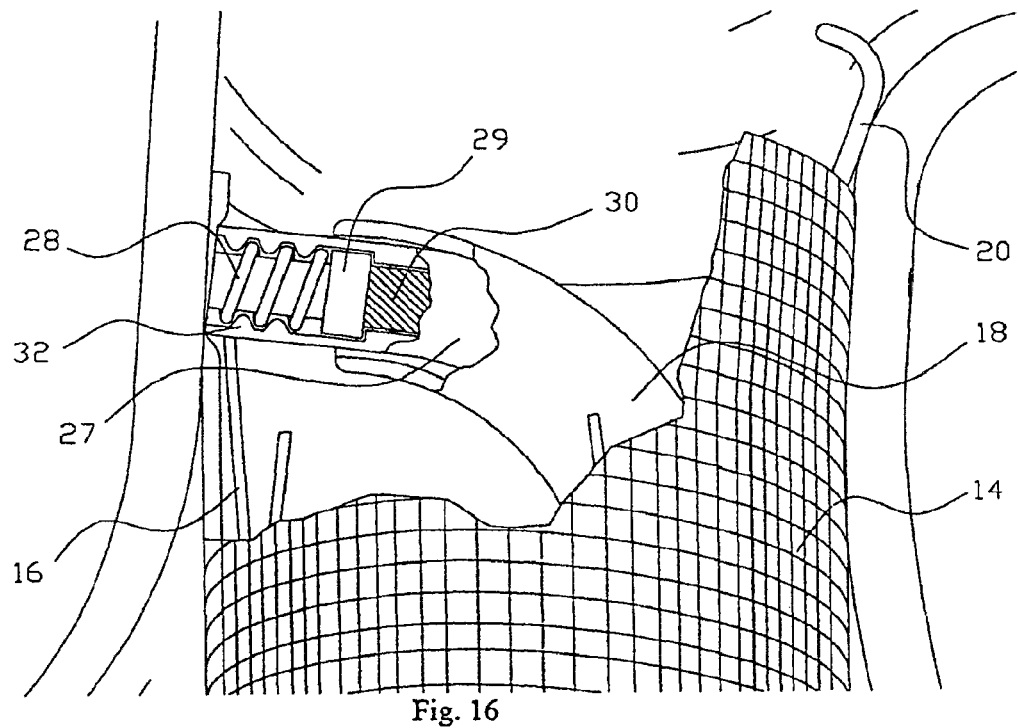
FIG. 16 is an enlarged cross-sectional view of one embodiment of the fastener applier of FIG. 14.
Figure 17:
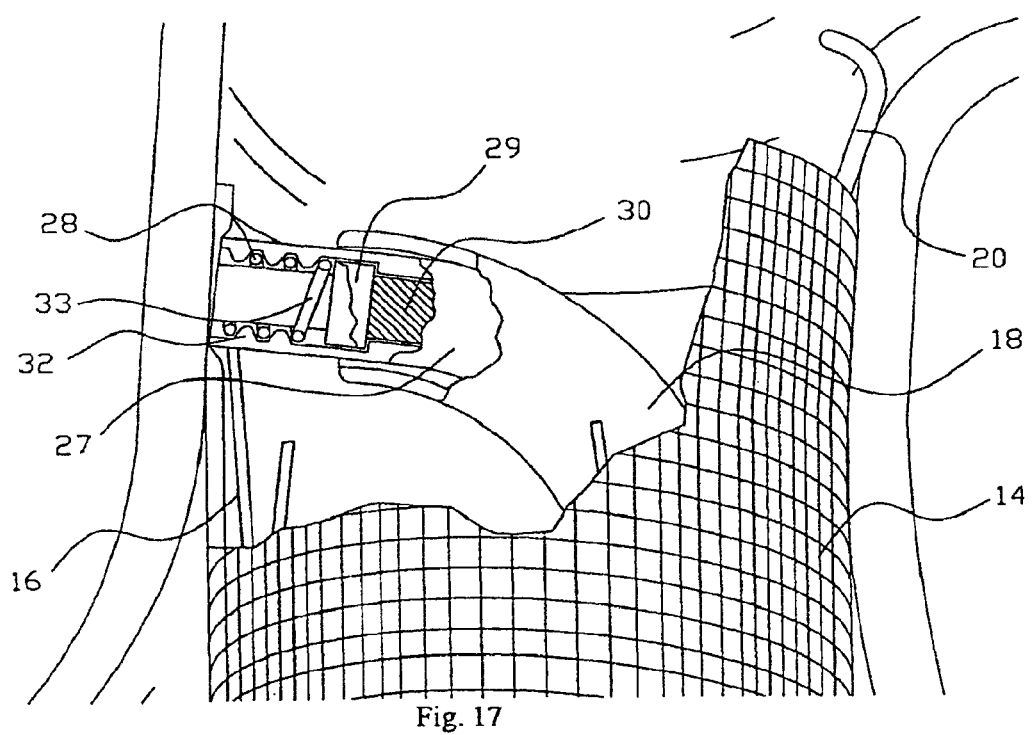
FIG. 17 is an enlarged cross-sectional view of the attachment applier showing one embodiment of the proximal end of the helical fastener and the drive mechanism.

FIG. 16 is an enlarged cross-sectional view of fastener applier 27 and directing device 18. In one embodiment of the fastener applier the helical fastener 28 is rotated via a fastener driver 29 through a drive shaft 30 that is connected to the control assembly 31. The drive shaft 30 can be made of any material that allows for both bending and rotation. The drive shaft is connected to the fastener driver 29, which engages and imparts torque to the helical fastener. FIG. 16 illustrates the coils of the helical fastener 28 engaged with internal grooves 32 within the fastener applier. It is contemplated that the grooves could be positioned along the entire length of the fastener or within a portion of its length. FIG. 17 is an enlarged cross-sectional view of the fastener applier 27 with a cross-section of the fastener driver 29 depicting one embodiment of engagement between the fastener driver and helical fastener 28. In this embodiment the proximal coil of the helical fastener is formed to produce a diagonal member 33, which crosses the diameter of the helical fastener. Similar helical fasteners are described in U.S. Pat. Nos. 5,964,772; 5,824,008; 5,582,616; and 6,296,656, the full disclosures of which are incorporated herein by reference.

Figure 18:
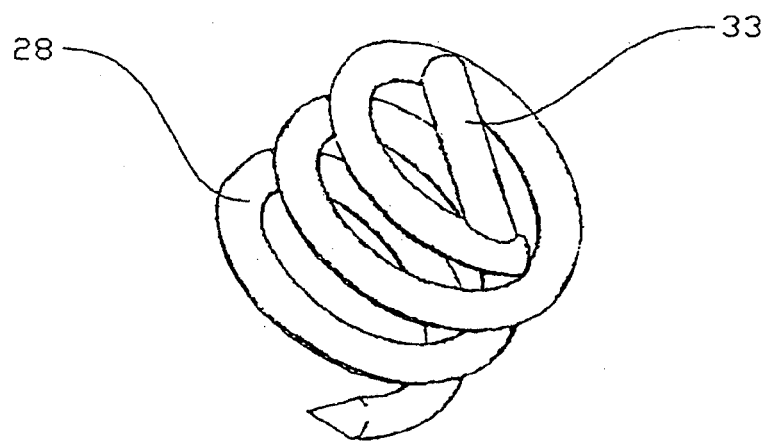
FIG. 18 is a enlarged perspective view of one embodiment of the helical fastener of FIG. 16.
Figure 19:
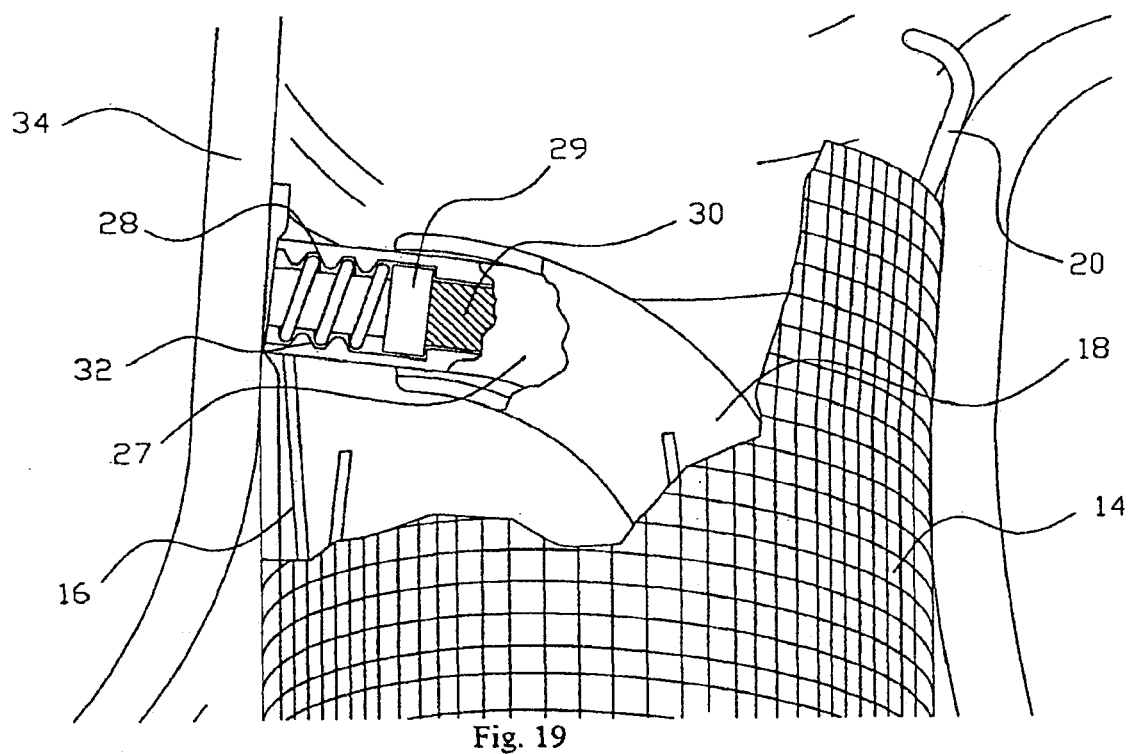
FIG. 19 is an enlarged view of the attachment applier showing one embodiment of the control assembly that activates the fastener applier.
Figure 20:
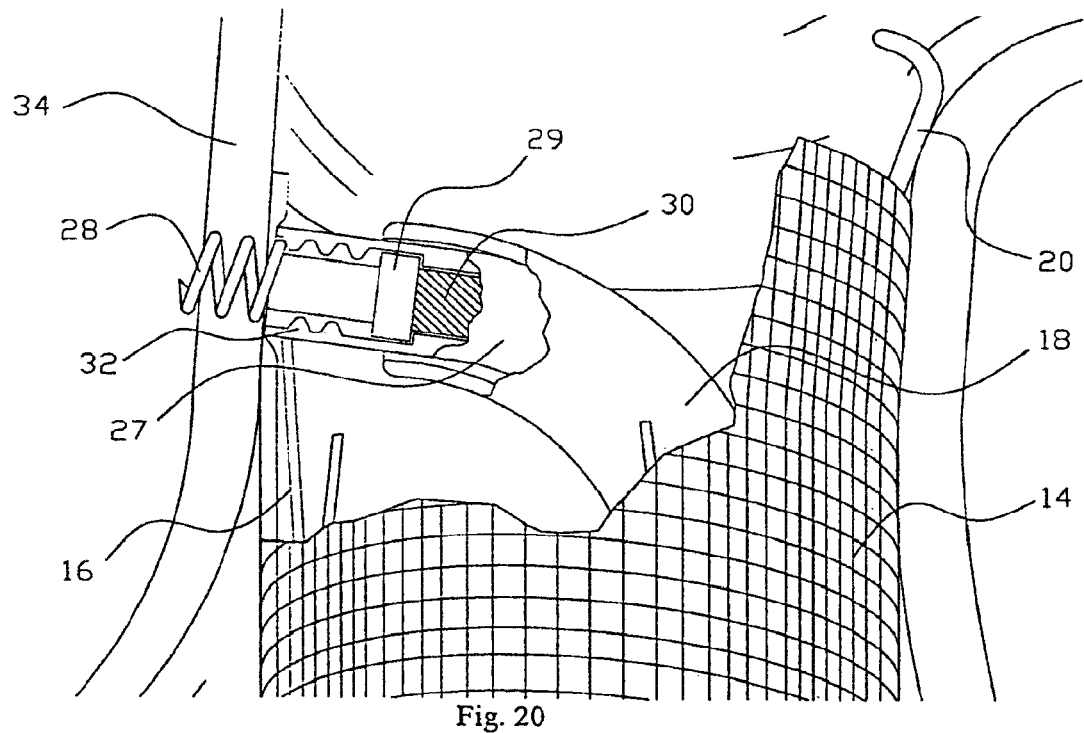
FIG. 20 is an enlarged view of the attachment applied activated with a fastener implanted into the graft and vessel wall.

FIG. 18 depicts one embodiment of the helical fastener 28 showing the diagonal member 33. FIG. 19 depicts one embodiment of the fastener applier 27 during activation of the fastener applier control assembly. Activation of the control assembly rotates the drive shaft, faster driver and helical fastener. This rotation causes the helical fastener 28 to travel within the internal grooves 32 of the fastener applier and into the graft 14 and vessel wall 34 FIG. 20. It is contemplated that the control assembly for the fastener applier could be activated mechanically, electrically, hydraulically or pneumatically.

Figure 21:
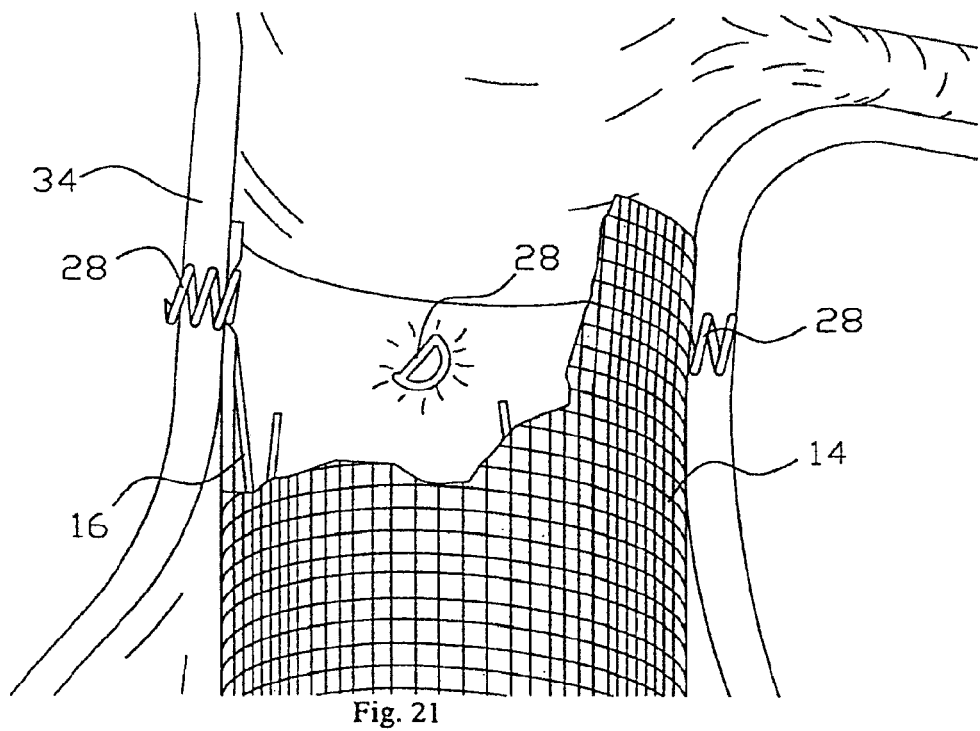
FIG. 21 is an enlarged view of the completed attachment of the proximal graft of FIG. 3 to the vessel wall with fasteners.

FIG. 21 illustrates a completed helical fastener 28 attachment of the graft 14 to the vessel wall 34. It is contemplated that one or more fasteners will be required to provide secure attachment of the graft to the vessel wall.

Figure 22:
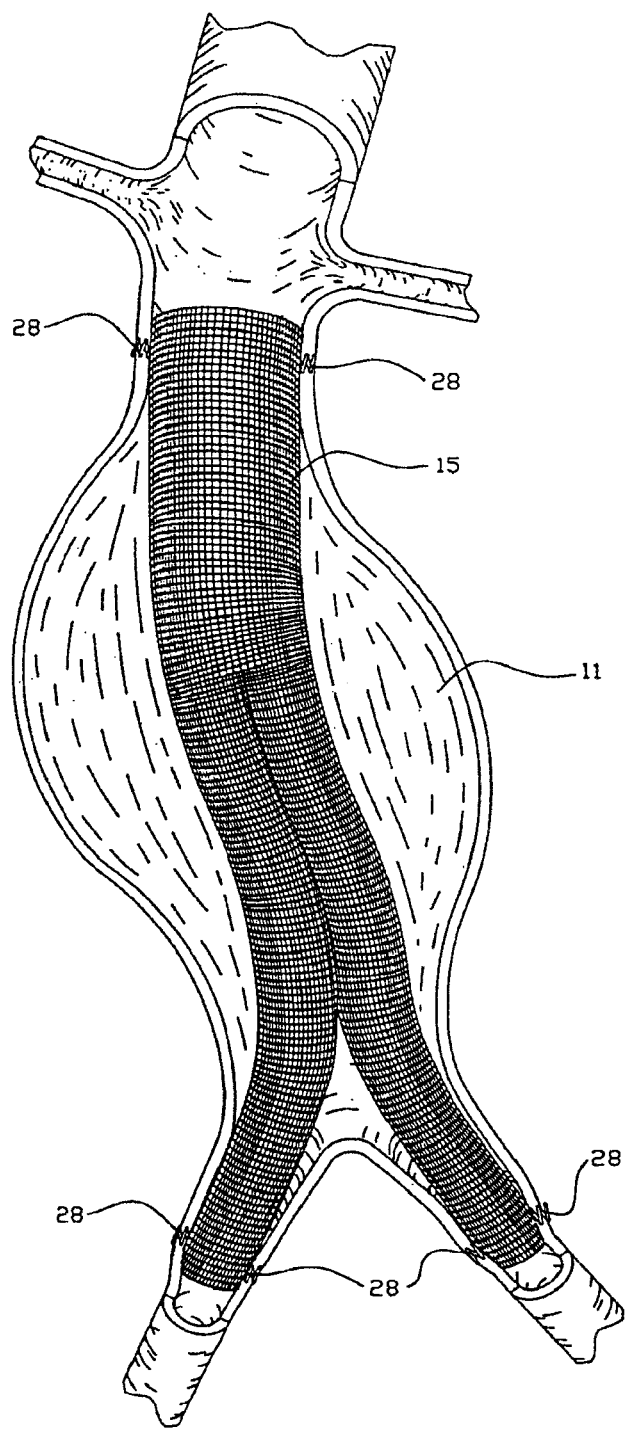
FIG. 22 is a perspective view of the graft of FIG. 4 completely attached to the vessel.

FIG. 22 illustrates a perspective view of a graft prosthesis attached to the vessel wall both proximally and distally. It is contemplated that the present invention can be used for graft attachment of both straight and bifurcated grafts 15 within the aorta and other branch vessels.

It will be appreciated that the components and/or features of the preferred embodiments described herein may be used together or separately, while the depicted methods and devices may be combined or modified in whole or in part. It is contemplated that the components of the directing device, fastener applier and helical fastener may be alternately oriented relative to each other, for example, offset, bi-axial, etc. Further, it will be understood that the various embodiments may be used in additional procedures not described herein, such as vascular trauma, arterial dissections, artificial heart valve attachment and attachment of other prosthetic device within the vascular system and generally within the body.

The preferred embodiments of the invention are described above in detail for the purpose of setting forth a complete disclosure and for the sake of explanation and clarity. Those skilled in the art will envision other modifications within the scope and sprit of the present disclosure.

What is claimed is:

1. A system comprising:
   an intraluminal directing device sized and configured for introduction from a remote access site to a location within a blood vessel lumen, the intraluminal directing device including a deflectable distal region sized and configured for manipulation to orient the distal region with respect to different desired fastening sites within the blood vessel lumen;
   a single helical tissue-piercing fastener having a proximal diagonal component extending across the diameter of the helical tissue-piercing fastener; and
   an intraluminal fastener applier including a driven component, a distal end of the intraluminal fastener applier comprising a lumen configured to receive the helical tissue-piercing fastener, the intraluminal fastener applier having internal helical grooves positioned along the entire length of the helical tissue-piercing fastener, the distal end of the driven component comprising a fastener driver, a first portion of which is positioned proximal to and immediately adjacent the helical grooves and the helical tissue-piercing fastener and is sized such that the helical tissue-piercing fastener cannot move proximally past the fastener driver within the lumen of the intraluminal fastener applier and a second portion of which is configured to engage the proximal diagonal component of the tissue-piercing fastener, the driven component being rotatable within the lumen to cause the helical tissue-piercing fastener to rotate along the internal helical grooves of the lumen and out of the distal end of the intraluminal fastener applier, and the intraluminal fastener applier being sized and configured to be introduced along the intraluminal directing device.

2. A system according to claim 1 wherein a desired plurality of tissue-piercing fasteners are introduced one fastener at a time in a circumferentially spaced-apart pattern at the different desired fastening sites within the blood vessel lumen.

3. A system according to claim 1 wherein the intraluminal directing device is sized and configured for rotation in concert with deflecting the distal region.

4. A system according to claim 1 wherein the intraluminal directing device includes a passage accommodating the intraluminal fastener applier.

5. A system comprising:
a prosthesis sized and configured for deployment within a blood vessel lumen,
an intraluminal directing device sized and configured for introduction from a remote access site to a location within the prosthesis, the intraluminal directing device including a deflectable distal region sized and configured for manipulation to orient the distal region with respect to different desired fastening sites to secure the prosthesis within the blood vessel lumen;
a single helical tissue-piercing fastener having a proximal diagonal component extending across the diameter of the helical tissue-piercing fastener; and
an intraluminal fastener applier including a driven component, a distal end of the intraluminal fastener applier comprising a lumen configured to receive the helical tissue-piercing fastener, the intraluminal fastener applier having internal helical grooves positioned along the entire length of the helical tissue-piercing fastener, the distal end of the driven component comprising a fastener driver, a first portion of which is positioned proximal to and immediately adjacent the helical grooves and the helical tissue-piercing fastener and is sized such that the helical tissue-piercing fastener cannot move proximally past the fastener driver within the lumen of the intraluminal fastener applier and a second portion of which is configured to engage the proximal diagonal component of the tissue-piercing fastener, the driven component being rotatable within the lumen to cause the helical tissue-piercing fastener to rotate along the internal helical grooves of the lumen and out of the distal end of the intraluminal fastener applier, and the intraluminal fastener applier being sized and configured to be introduced along the intraluminal directing device.

6. A system according to claim 5 wherein a desired plurality of tissue-piercing fasteners are introduced one fastener at a time in a circumferentially spaced-apart pattern at the different desired fastening sites to secure the prosthesis to the blood vessel lumen.

7. A system according to claim 5 wherein the intraluminal directing device is sized and configured for rotation in concert with deflecting the distal region.

8. A system according to claim 5 wherein the intraluminal directing device includes a passage accommodating the intraluminal fastener applier.

9. The system according to claim 1, wherein the fastener driver comprises:
the second portion extending distally from the first portion, wherein the second portion is configured to be received within at least a portion of the helical tissue-piercing fastener.

10. The system according to claim 9,
wherein a proximal end of the helical tissue-piercing fastener comprises the proximal diagonal component, and
wherein the second portion of the fastener driver is configured to engage the proximal diagonal component to drive the helical tissue-piercing fastener out of the distal end of the intraluminal fastener applier.

11. The system according to claim 5, wherein the fastener driver comprises:
the second portion extending distally from the first portion, wherein the second portion is configured to be received within at least a portion of the helical tissue-piercing fastener.

12. The system according to claim 5,
wherein a proximal end of the helical tissue-piercing fastener comprises the proximal diagonal component, and
wherein the second portion of the fastener driver is configured to engage the proximal diagonal component to cause the helical tissue-piercing fastener to rotate along the internal helical grooves of the lumen and out of the distal end of the intraluminal fastener applier.

* * * * *